US012558508B2

(12) United States Patent
Kane

(10) Patent No.: US 12,558,508 B2
(45) Date of Patent: Feb. 24, 2026

(54) NASAL RESPIRATORY APPARATUS

(71) Applicant: Pneuma Therapeutics, Inc., Tucson, AZ (US)

(72) Inventor: David M. Kane, Windham, NH (US)

(73) Assignee: Pneuma Therapeutics, Inc., Tucson, AZ (US)

( * ) Notice: Subject to any disclaimer, the term of this patent is extended or adjusted under 35 U.S.C. 154(b) by 863 days.

(21) Appl. No.: 17/792,689

(22) PCT Filed: Jan. 13, 2021

(86) PCT No.: PCT/US2021/013192
§ 371 (c)(1),
(2) Date: Jul. 13, 2022

(87) PCT Pub. No.: WO2021/146249
PCT Pub. Date: Jul. 22, 2021

(65) Prior Publication Data
US 2023/0044155 A1      Feb. 9, 2023

Related U.S. Application Data

(60) Provisional application No. 62/960,385, filed on Jan. 13, 2020.

(51) Int. Cl.
A61M 16/06          (2006.01)
A61M 16/08          (2006.01)

(52) U.S. Cl.
CPC ...... A61M 16/0666 (2013.01); A61M 16/085 (2014.02); A61M 2230/432 (2013.01)

(58) Field of Classification Search
CPC ...................................... A61M 16/0666–0677
See application file for complete search history.

(56) References Cited

U.S. PATENT DOCUMENTS

| | | | | | |
|---|---|---|---|---|---|
| 1,192,186 | A | * | 7/1916 | Greene | ................. A61M 16/06 |
| | | | | | 128/207.13 |
| 8,210,182 | B2 | * | 7/2012 | Duquette | .............. A61M 16/00 |
| | | | | | 128/207.18 |

(Continued)

FOREIGN PATENT DOCUMENTS

| | | | | |
|---|---|---|---|---|
| WO | WO-2014092703 A1 | * | 6/2014 | ........ A61M 16/0688 |
| WO | 2020132664 | | 6/2020 | |
| WO | 2021/146249 | | 7/2021 | |

OTHER PUBLICATIONS

International Search Report and Written Opinion, dated Apr. 12, 2021, in connection with International Application No. PCT/US2021/013192.

(Continued)

*Primary Examiner* — Bradley H Philips
(74) *Attorney, Agent, or Firm* — Meunier Carlin & Curfman LLC

(57) ABSTRACT

A nasal respiratory apparatus comprising a compressible nasal dam is removably engaged with an air chamber to provide respiratory gas to a patient. The air chamber has a gas connection port, at least one nasal conduit, a nasal end tidal sample port, wherein the gas connection port is configured to receive an externally supplied gas via a gas supply tube and wherein the at least one nasal conduit in fluid communication with the gas connection port. The nasal dam has a least one nares port corresponding to the at least one nasal conduit of the air chamber, the nares port extending from an upper external surface of the nasal dam to a lower external surface of the nasal dam such that the upper external surface of the nasal dam interfaces with soft tissue of a patients nasal base to provide a substantial seal around the patients nasal base to facilitate respiratory gas supply to the patient.

30 Claims, 30 Drawing Sheets

(56) References Cited

U.S. PATENT DOCUMENTS

| | | | |
|---|---|---|---|
| 2004/0261797 A1* | 12/2004 | White | A61M 16/0003 |
| | | | 128/206.11 |
| 2006/0137690 A1* | 6/2006 | Gunaratnam | A61M 16/0666 |
| | | | 128/207.18 |
| 2007/0125379 A1* | 6/2007 | Pierro | A61M 16/0666 |
| | | | 128/204.23 |
| 2009/0044808 A1 | 2/2009 | Guney et al. | |
| 2010/0313891 A1 | 12/2010 | Veliss et al. | |
| 2012/0080033 A1* | 4/2012 | Varga | A61M 16/0672 |
| | | | 128/204.18 |
| 2013/0284176 A1* | 10/2013 | Dickerson | A61M 16/0683 |
| | | | 128/204.18 |
| 2016/0213281 A1* | 7/2016 | Eckerbom | A61M 16/0672 |
| 2019/0217036 A1 | 7/2019 | Spear et al. | |
| 2020/0023153 A1* | 1/2020 | Chou | A61M 16/0816 |
| 2023/0405255 A1* | 12/2023 | Kane | A61M 16/0622 |

OTHER PUBLICATIONS

International Preliminary Report on Patentability issued PCT/US2021/013192, dated Jul. 28, 2022.

* cited by examiner

Front View

Right Side View

Exhaled Gas

Inhaled Gas

Section B - B

Section A - A

Front View

Right Side View

NASAL RESPIRATORY APPARATUS

CROSS REFERENCE TO RELATED APPLICATIONS

This application is claims priority to U.S. Provisional Patent Application Ser. No. 62/960,385, filed Jan. 13, 2020, which application is hereby incorporated by this reference in its entirety.

BACKGROUND

Field

Embodiments of the present invention relate to oxygenation, ventilation and end tidal carbon dioxide ($CO_2$) sampling during general anesthesia and deep sedation, and specifically to a nasal mask with various related features.

Background

General anesthesia has historically utilized a full-face mask attached to an anesthesia machine to support providing anesthetic gases and oxygen, as well as ventilating the patient and monitoring exhaled end tidal $CO_2$ levels. A major issue with using a full-face mask is that the mask must be removed for oral access to place an intubation tube, resulting in an apenic period. Respiratory compromise is a common result from the apenic period for high-risk patients.

Given the trend for more minimally invasive procedures, the use of intravenous deep sedation has grown significantly. Nasal cannula are used providing nasal oxygenation, but do not provide pressurization, sometimes resulting in respiratory compromise if the nasal pharynx becomes blocked.

To address the shortcomings of full-face masks and nasal cannula, nasal ventilation masks covering the nose and sealing against the face are becoming popular. nasal ventilation masks support pressurization required to overcome blockage of the nasal pharynx, but obstruct the region near the eyes, easily lose a seal if the mask is tilted or if there is facial hair such as a mustache is present.

A nasal respiratory apparatus according to principles described herein and its various embodiments and combinations of features addresses the major shortcomings of all three of these approaches, supporting pressurized oxygenation, ventilation and end-tidal CO2 sampling via nasal ventilation system that seals via the nares and nasal vestibule. This results in a more secure seal. The device is much more compact an unobtrusive than either mask approach, allowing for oral and eye access if required.

BRIEF SUMMARY OF THE DISCLOSURE

Accordingly, the present invention is directed to nasal respiratory apparatus that obviates one or more of the problems due to limitations and disadvantages of the related art.

In accordance with the purpose(s) of this invention, as embodied and broadly described herein, this invention, in one aspect, relates to a nasal respiratory apparatus comprising an air chamber having a gas connection port, at least one nasal conduit, a nasal end tidal sample port, wherein the gas connection port is configured to receive an externally supplied gas via a gas supply tube and wherein the at least one nasal conduit in fluid communication with the gas connection port; and a nasal dam having a least one nares port corresponding to the at least one nasal conduit of the air chamber, the nares port extending from an upper external surface of the nasal dam to a lower external surface of the nasal dam such that the upper external surface of the nasal dam interfaces with soft tissue of a patient's nasal base to provide a substantial seal around the patient's nasal base.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

Further embodiments, features, and advantages of the nasal respiratory apparatus, as well as the structure and operation of the various embodiments of the nasal respiratory apparatus, are described in detail below with reference to the accompanying drawings.

It is to be understood that both the foregoing general description and the following detailed description are exemplary and explanatory only, and are not restrictive of the invention as claimed.

BRIEF DESCRIPTION OF THE DRAWINGS

The accompanying figures, which are incorporated herein and form part of the specification, illustrate a new nasal respiratory apparatus. Together with the description, the figures further serve to explain the principles of the new nasal respiratory apparatus described herein and thereby enable a person skilled in the pertinent art to make and use the new nasal respiratory apparatus.

DETAILED DESCRIPTION

Reference will now be made in detail to embodiments of the new nasal respiratory apparatus with reference to the accompanying figures. For convenience of explanation, various figures make use of a right-handed X, Y, Z-axis Cartesian Coordinate system reference space, with reference to X-Y, X-Z, and Y-Z planes.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

This present disclosure relates to a nasal respiratory platform supporting pressurized nasal oxygenation, ventilation, and expired End Tidal CO2 (carbon dioxide) sampling by interfacing with and sealing about the nasal base of the nose. Details of various embodiments of the nasal respiratory apparatus are provided herein.

This nasal respiratory apparatus is described in the following.

Figure 1A:
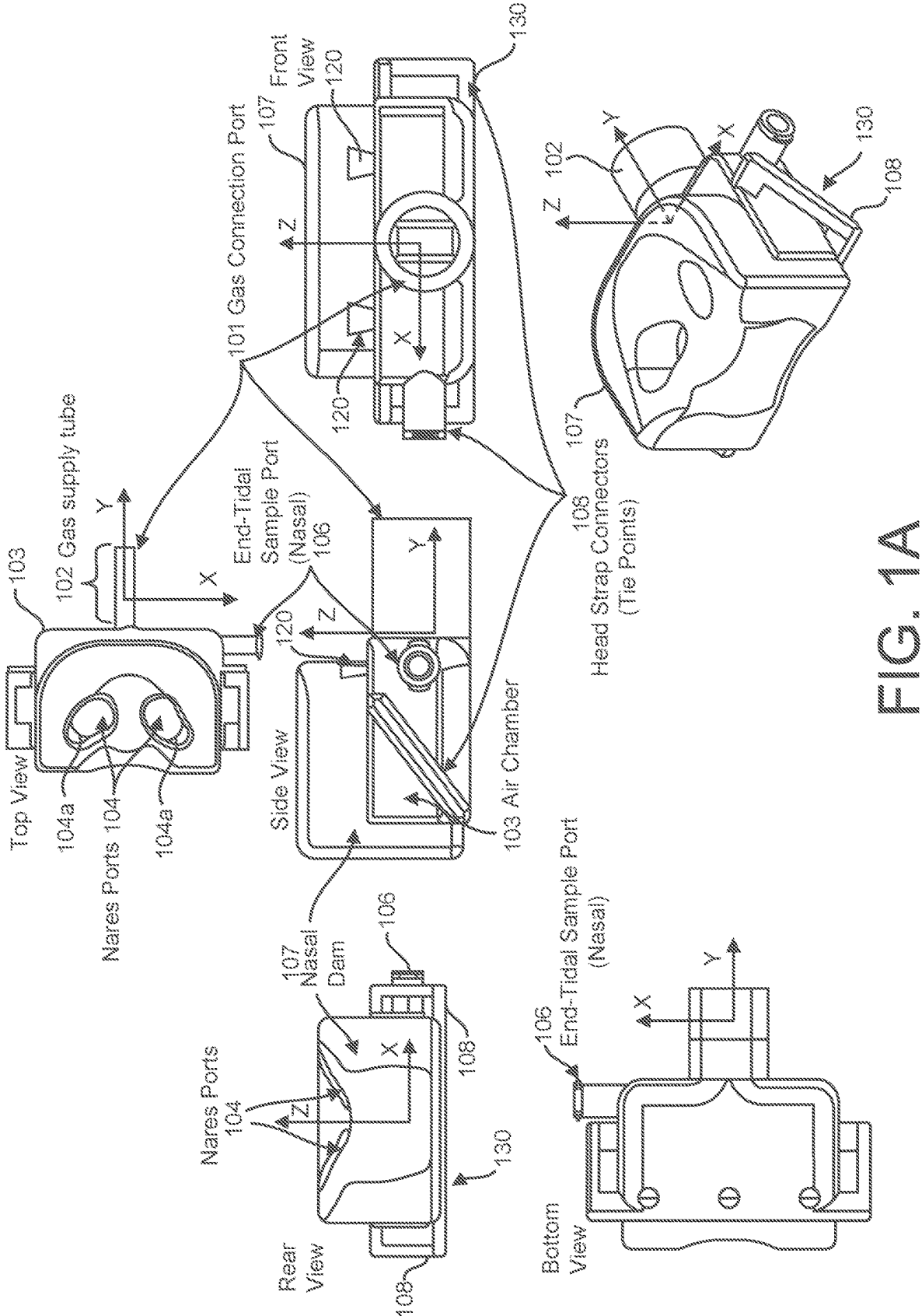
FIG. 1A illustrates elements of a nasal respiratory apparatus according to principles described herein.
Figure 1B:
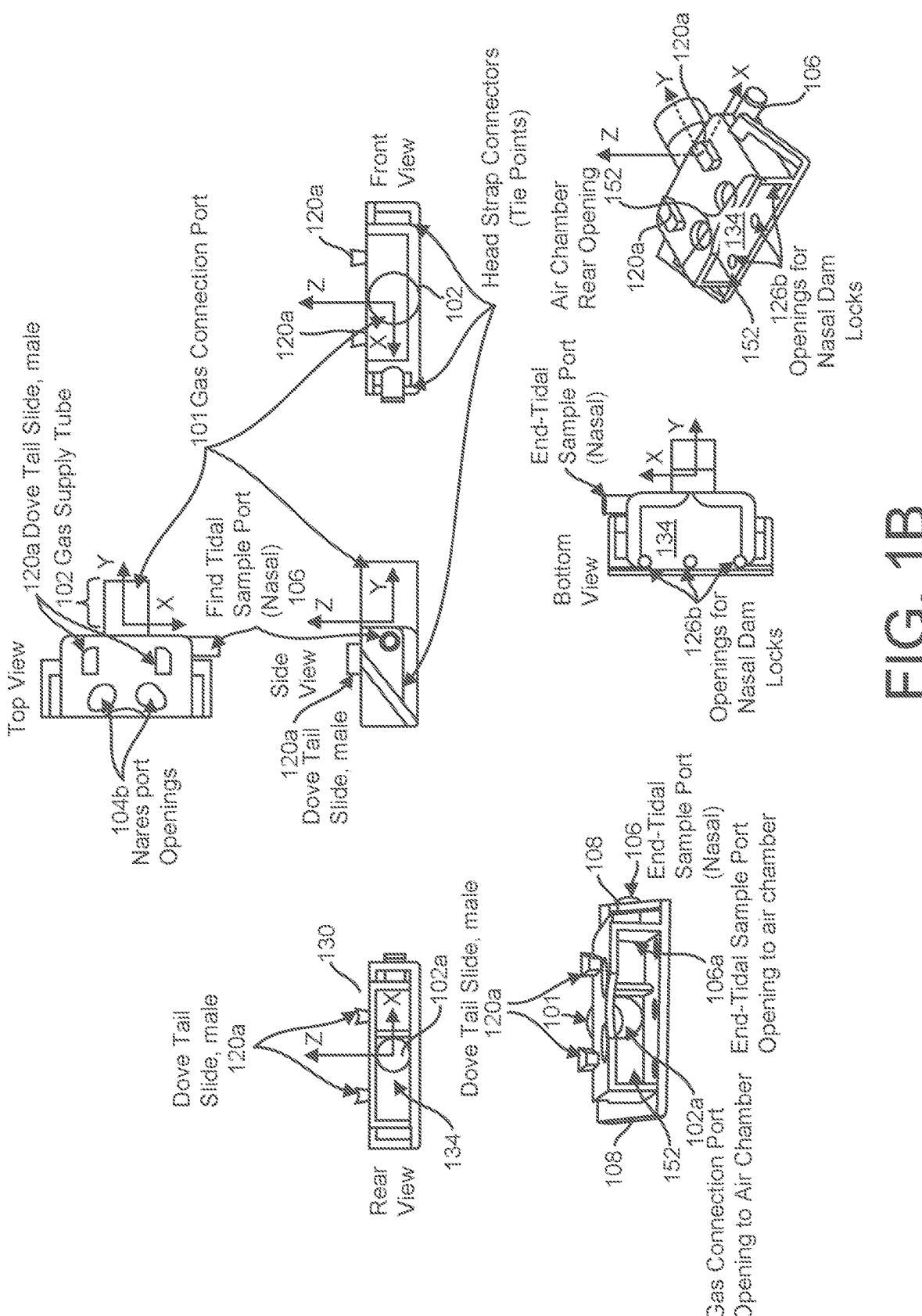
FIG. 1B illustrates elements of an exemplary air chamber as illustrated in FIG. 1A.
Figure 1C:
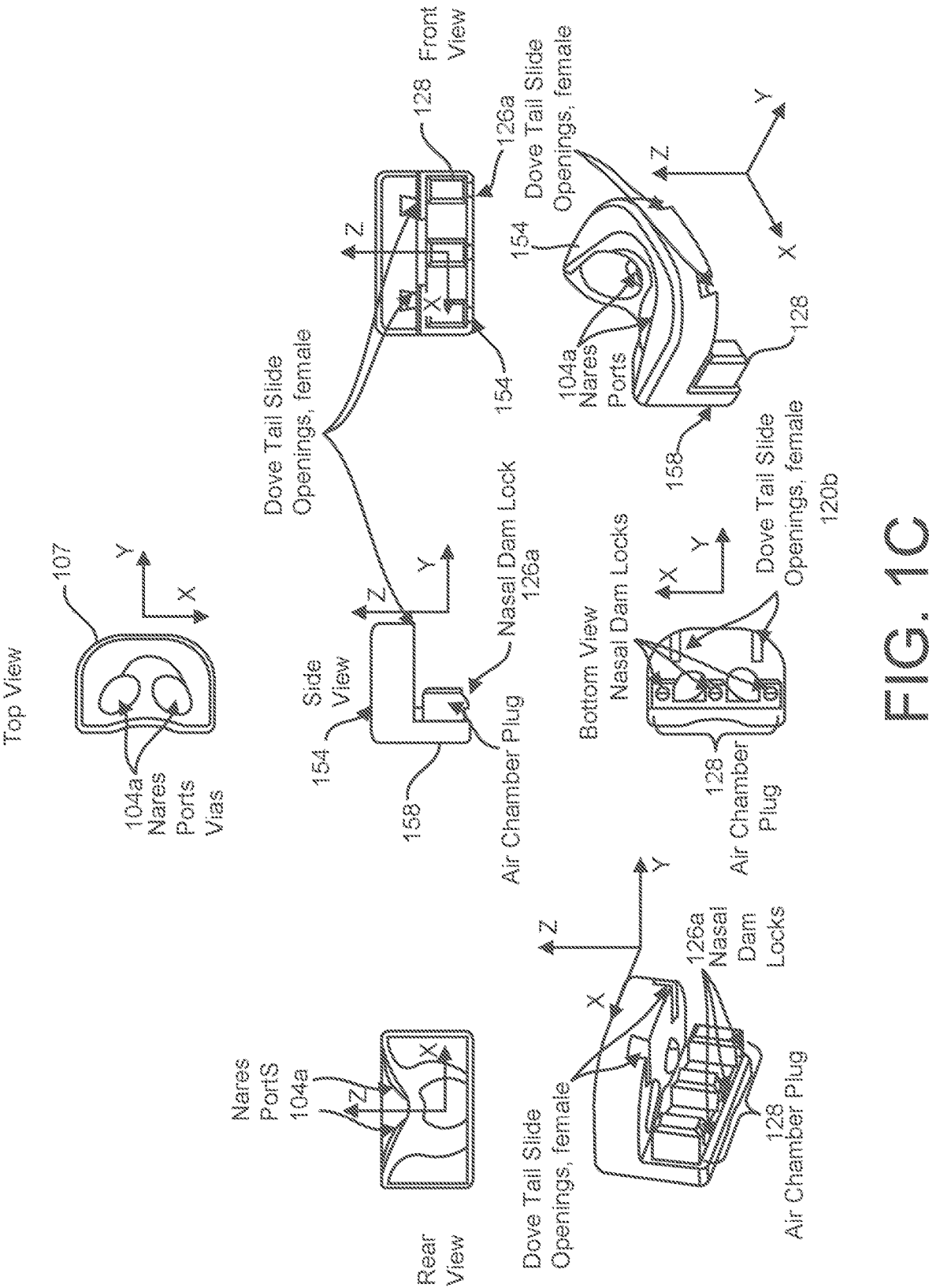
FIG. 1C illustrates elements of an exemplary nasal dam as illustrated in FIG. 1A

The nasal respiratory apparatus includes a Nasal dam 107 that interfaces with the nasal base and an Air chamber 103 that interfaces with the gas source (not shown) and end tidal CO2 sampling line (not shown), which is illustrated in an assembled state in FIG. 1A. FIG. 1B illustrates the air chamber structure 130 separated from the nasal dam 107. FIG. 1C illustrates the nasal dam 107 separated from the air chamber structure 130.

As illustrated in FIG. 1A, a gas supply tube 102 extends from a front end wall 148 of the air chamber 103 and acts as a conduit containing and allowing for the flow of gas between the gas connection port 101 and an interior cavity 134 of an air chamber 103. A gas connection port 101 at the end of the gas supply tube 102 provides an interface, which may be a standard conical connector, for example, a 15 mm conical connector in compliance with ISO 5356-1(E) or the like. Other connector configurations may be possible. The air chamber 103 provides a structural and a gas flow interface between the gas supply tube 102, nares port or ports 104, and an end tidal sampling port 106. The assembly of the nasal dam 107 and the air chamber 103 may include one or two nares ports 104 to provide a mechanical and gas flow interface between a patient's nares (not shown) and the gas supply/source (not shown) via the air chamber 103 and between the patient's nares and the end tidal sampling port 106. In use, in the nasal respiratory assembly according to principles described herein, the nasal dam 107 surrounds the nares ports 104 and interfaces with soft tissue of a patient's nasal base, providing a pressure seal in order to contain air flow between the patient's nasal pharynx and the nasal respiratory apparatus of any of the embodiments described herein. The nasal dam 107 includes vias 104a that, when the nasal dam 107 is placed on the air chamber 103, align with the nares ports 104 of the air chamber 103, allowing for air flow between the patient's nares and the air chamber 103.

The end tidal sampling port 106 as illustrated in FIG. 1A is a nasal end tidal sample port. The nasal end tidal sample port, in the context of the illustration, is parallel to the X-axis, and provides for the sampling of exhaled end tidal carbon dioxide ($CO_2$). As one example, the end tidal sample port exterior may be a standard connector, such as a female luer slip connector per ISO 80396-7: 2016(E). Other connector configurations may be possible. While illustrated in FIG. 1A as extending from a side wall of the air chamber structure 130, the end tidal sample port may extend from any appropriate location. Any embodiment disclosed herein may include an oral end tidal sampling configuration according to any described herein, including an oral end tidal scoop.

Figure 3:
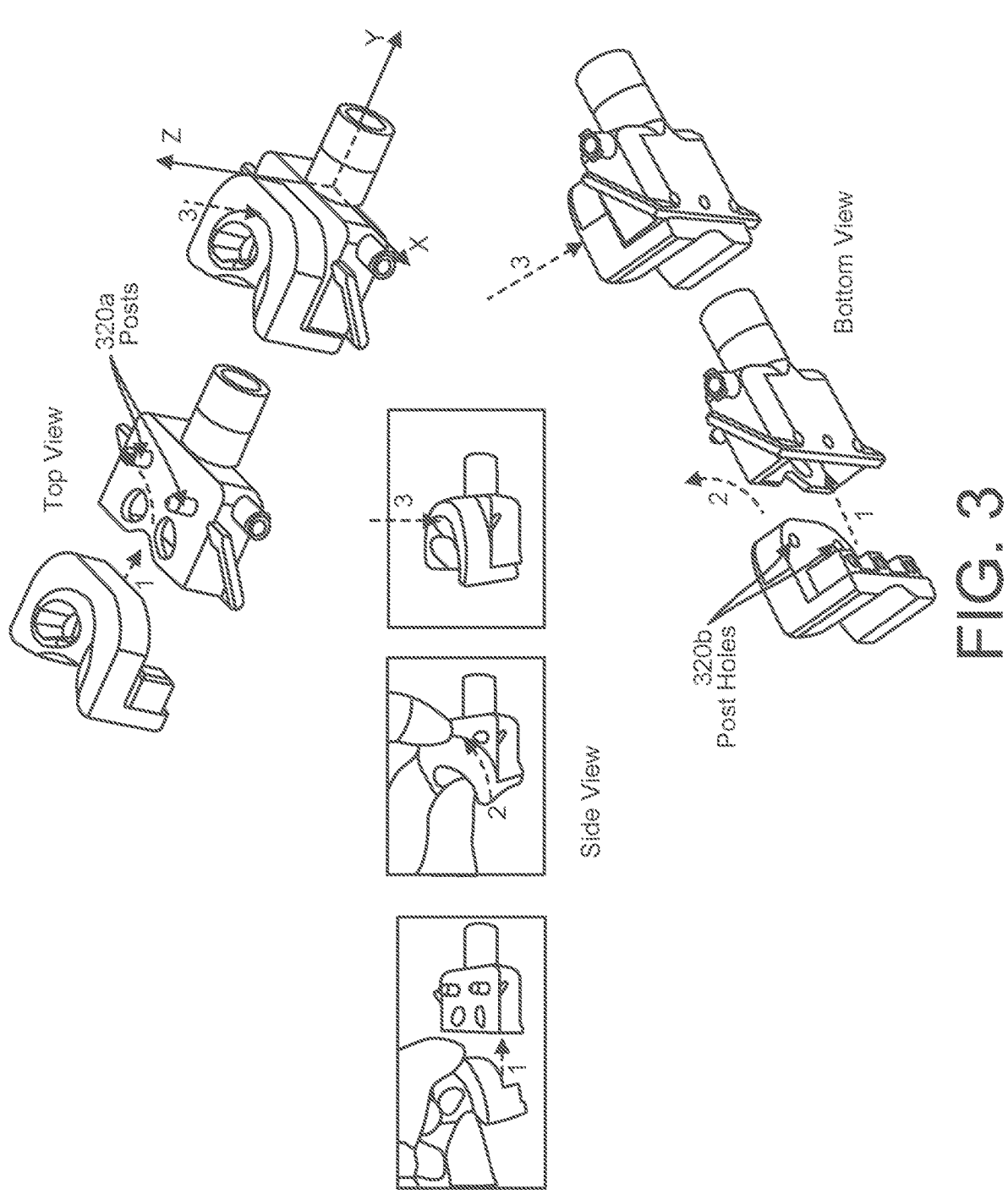
FIG. 3 illustrates engagement of an exemplary nasal dam with an exemplary air chamber having engagement posts.

As illustrated in FIG. 1A, the nasal dam 107 may connect to an exterior side of the upper wall 138 of the air chamber 103 via a dovetail joint 120. As illustrated in FIG. 1A, in one aspect, one or more tapered tenons (male connector) 120a may extend or project from the exterior side of the upper wall 138 of the air chamber 103. The nasal dam 107 includes complementary notches or recesses (female connector) 120b positioned on an underside of the nasal dam 107 to align with the one or more tapered tenons extending from the upper wall 138 of the air chamber 103. The nasal dam 107 may be abutted to the air chamber 103 by engaging the tenons on the air chamber 103 with the notches or recesses in the nasal dam 107 (while aligning the nasal dam vias 104a with the nares ports 104 of the air chamber 103). Multiple dovetail joints 120 can be replaced by a single dovetail without limitation. In at least one configuration disclosed herein, the dovetail joints 120 may be replaced by posts and corresponding post holes, as illustrated in FIG. 3.

Referring to FIG. 1B, the air chamber 103 generally includes an air chamber structure 130 that defines an air chamber cavity 134. The air chamber structure 130 includes an upper wall 138 and a lower wall 142 parallel to an X-Y plane, two side walls 144 parallel to a Y-Z plane and a front end wall 148 parallel to an X-Z plane. The upper wall 138 of the air chamber 103 includes at least one nares port opening(s) 104b. The gas supply tube 102 may extend from any of the walls of the air chamber structure 130, but is illustrated in FIG. 1B as extending from the front wall of the air chamber structure 130. The gas supply tube 102 may be integrally formed with the air chamber 103 and a lumen 102a of the gas supply tube 102 is fluidically coupled with the air chamber cavity 134 such that when gas is supplied through the gas supply tub, gas flows from the gas supply tube 102 into the air chamber cavity 134. As illustrated in FIG. 1B, the air chamber structure 130 also includes a rear opening 152 opposite the front end wall 148 exposing the air chamber cavity 134. As described and illustrated herein, the air chamber structure 130 may be described as being roughly "box shaped", however, the air chamber structure 130 is not necessarily so limited, and may have any appropriate cross-section within the spirit and scope of the invention, when in conjunction with a nasal dam, as described herein.

According to principles described herein, in an aspect, one or more male dovetail slides 120a extend/project from an exterior surface of the upper wall 138 of the air chamber 103. A front view of the dovetail looking down the Y axis, as illustrated in FIG. 1B, has a wider top than base that prevents motion of the Nasal dam 107 along the Z axis. Multiple dovetails can be replaced by a single dovetail.

The air chamber lower wall 142 may also include openings or detents 126b for receiving structures/projections 126a of the nasal dam therein. As can be appreciated, openings 126b would extend through the air chamber lower wall 142, while detents 126b would extend into the air chamber lower wall 142 from the air chamber cavity 134, and either structure may be used for receiving the nasal dam projections without departing from the spirit and scope of this disclosure. As described herein, the nasal dam 107 includes air chamber plugs 128 with nasal dam lock projections 126a that engage the rear opening 152 of the air chamber 103 to seal the air chamber rear opening 152. When the nasal dam 107 is abutted with the air chamber structure 130, the male dovetails 120a of the air chamber 103 engage one or more complementary dovetail recesses 120b on an underside of the nasal dam 107, such that, when the dovetail slide(s) 120a and the dovetail recess(es) 120b are engaged, vias 104a of the nasal dam 107 align with nares ports 104 that extend through the upper wall 138 of the air chamber 103 into the air chamber cavity 134. Projections 126a may extend from a portion of the air chamber plugs 128 and be complementary to the openings or detents 126b of the air chamber 128 to engage the openings or detents 126b. When engaged, the nasal dam 107 is locked to the air chamber 103 along the X and Z axes.

Additional elements of the Nasal dam 107 are illustrated in FIG. 1C, which illustrates a nasal dam according to principles described herein. As shown in FIG. 1C, the nasal dam 107 may include a nasal base portion 154 oriented generally in the X-Y plane and a nasal dam wall 158 extending in the X-Z plane from the nasal base. It is contemplated that the wall extends from an end of the nasal base portion 154 designed to be adjacent a patient's face such that a proximate face of the nasal dam wall 158 will be adjacent to or touch the patient's face and a distal face of the nasal dam wall 158 will abut a portion of the air chamber structure forming a perimeter of the rear opening 152 of the air chamber 103. The nasal dam of FIG. 1C includes air chamber plug(s) 128 extending from the distal face of the nasal dam wall 158 and which are configured to engage the rear opening 152 of the air chamber (air chamber rear opening 152, illustrated in FIGS. 1B and 2A). The air chamber plug(s) 128 act to seal the air chamber rear opening 152 when the nasal dam 107 and the air chamber 103 are engaged. Although illustrated in FIG. 1C as three separate projections, the air chamber plug 128 may be a single projection or any number of projections suitable for engaging and sealing the rear opening 152 of the air chamber 103. Similarly, although shown with each plug having a projection 126a of the nasal dam lock 126 extending therefrom, the plugs may have no nasal dam projection 126a or any suitable number sufficient to secure the air chamber plugs 128 in the air chamber cavity 134. While shown here with nasal dam locks, the air chamber plug(s) may be configured to provide a fit within the rear opening 152 of the air chamber 103 with sufficient friction or interference with respect to the inner surfaces of the walls of air chamber cavity 134 to hold the air chamber plug(s) within the rear opening 152 without the disclosed nasal dam locks.

As discussed above, the nasal dam 107 may optionally include one or more nasal dam locks 126 to secure the nasal dam 107 to the air chamber 103 along the Y-axis when the nasal dam 107 and the air chamber 103 are engaged. As illustrated in FIG. 1C, the nasal dam lock(s) 126 may be a projection 126a extending from the underside of at least one respective the air chamber plug 128. In the example illustrated in FIG. 1C, there are three air chamber plugs 128 each with a nasal dam lock 126 extending therefrom, but the number of air chamber plugs 128 and the number of air chamber plugs 128 having a nasal dam lock 126 is not limited by the illustrated embodiment. The air chamber structure 130 includes detents or openings 126b that correspond with a number of the nasal dam lock projections 126a sufficient to cause the nasal dam 107 to seat within the air chamber 103, with the nasal dam lock projections 126a extending into the respective recesses or detents 126b. It is contemplated that the number of air chamber detents 126b need not correspond exactly with the number of nasal dam lock projections 126.

The nasal dam may made of a soft material (e.g., Shore A 5-20 durometer), allowing the material to conform to and sufficiently seal the nasal base of the patient from a pressure differential between the air chamber interior and the atmosphere. The soft material may also assist the dovetail joint being formed by the interfacing of the nasal dam with the air chamber structure 130 and/or seal of the air chamber cavity rear opening 152 by the air chamber plugs 138 (which may extend from a wall 158 of the nasal dam that extends in the X-Z plane from a nasal base portion 154 of the nasal dam 107, where the nasal base portion 154 of the nasal dam 107 is oriented generally in the X-Y plane, such that the wall may abut the rear opening 152 of the air chamber 103).

A head strap may be connected to the nasal respiratory device via head strap connectors 108, which provide mechanical tie points between the nasal respirator apparatus and the head strap (not shown in FIG. 1A) that secures the nasal respiratory apparatus to the patient's head.

Figure 2A:
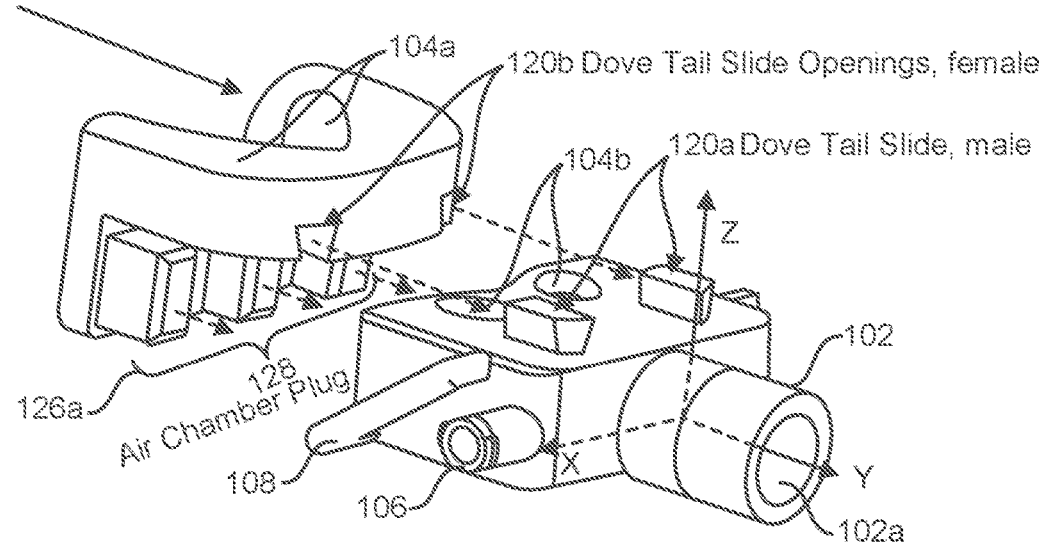
FIG. 2A illustrates engagement elements of the exemplary nasal dam with an exemplary air chamber having dovetails.
Figure 2A:
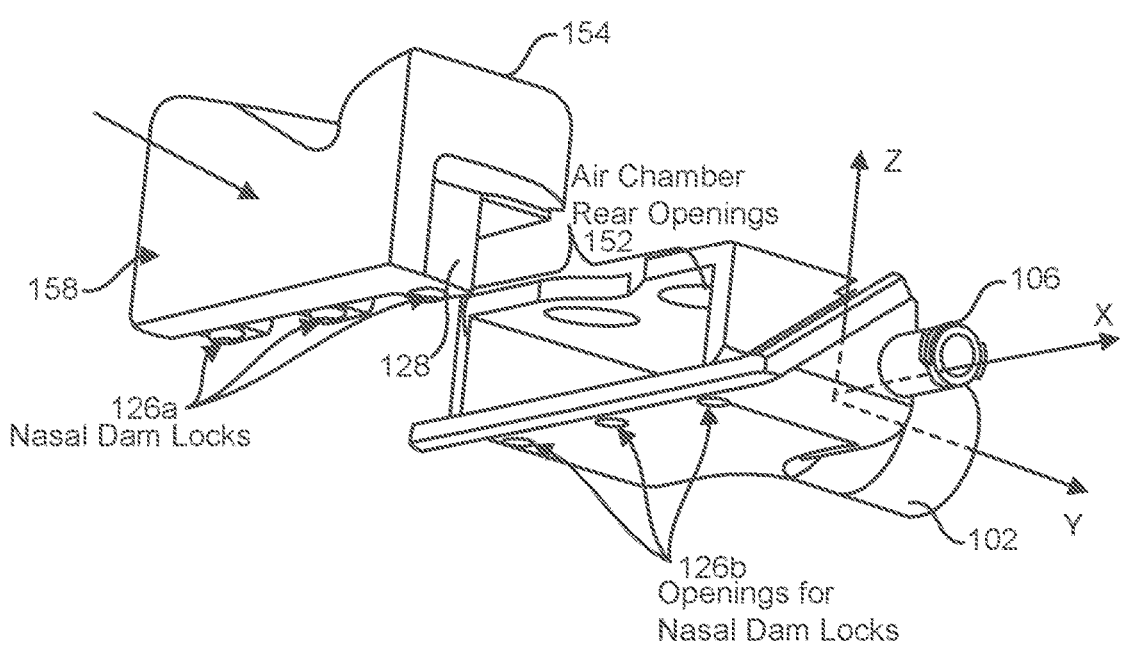
Figure 2B:
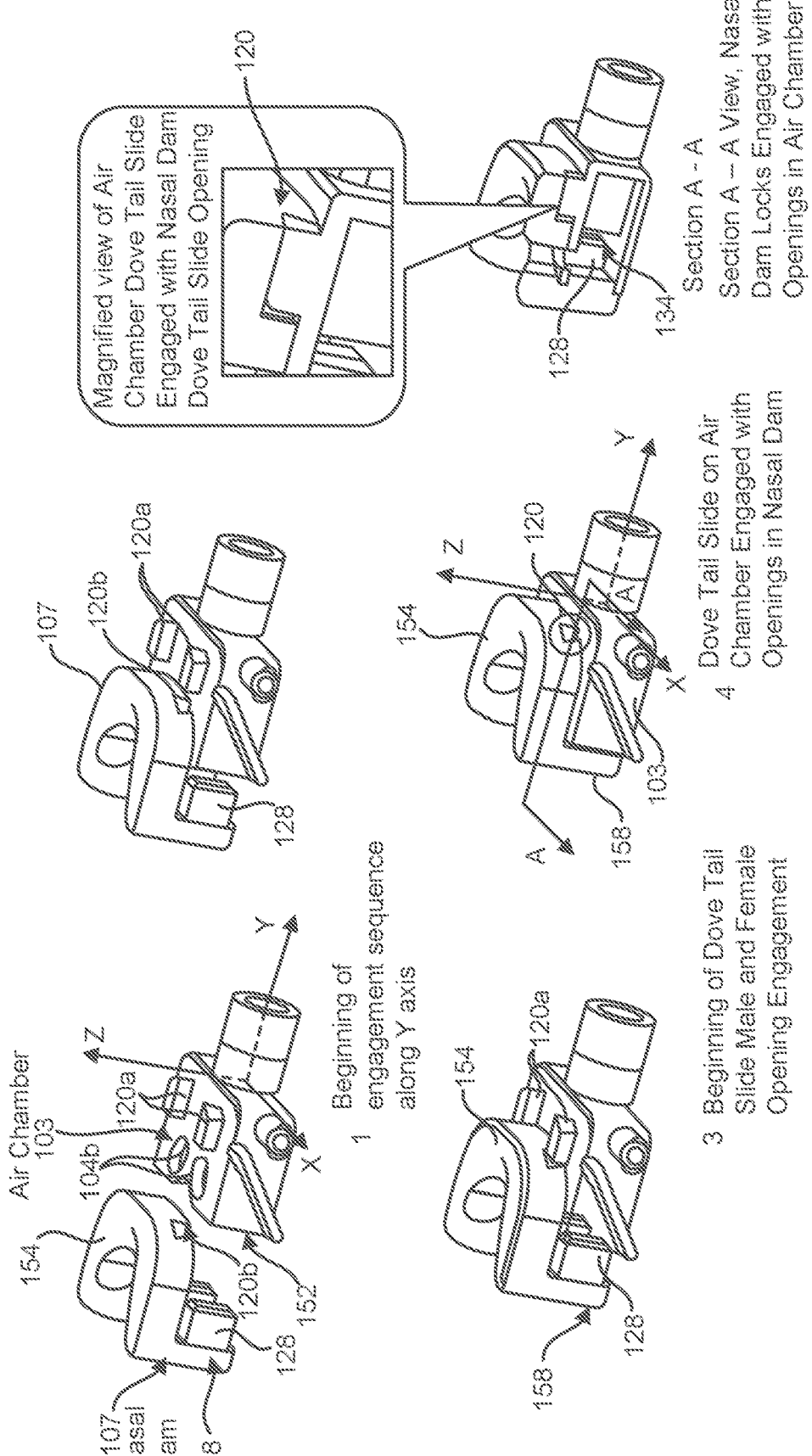
FIG. 2B illustrates a step sequence for engaging the nasal dam with the air chamber to achieve an exemplary nasal respiratory apparatus.

FIG. 2A illustrates assembly of the nasal dam 107 and the air chamber structure 130 to provide the nasal respiratory device according to principles described herein. For example, the Nasal dam 107 is secured to the Air chamber 103 by sliding the Nasal dam 107 relative to the Air chamber 103 along the Y axis until fully engaged as illustrated in FIG. 2A. Illustrated with respect to the dovetail configuration, the Nasal dam 107 to Air chamber 103 engagement sequence as it moves along the Y axis is illustrated in FIG. 2B with the dove tail slide being highlighted. Step 1 shows the beginning location of the Nasal dam 107 relative to the Air chamber 103. Step 2 shows the nasal dam 107 moving towards the Air chamber 103 along the Y axis. Step 3 shows the slide opening (notch) 120b of the Nasal dam 107 almost engaged with the slide (tenon) 120a on the Air chamber 103. Step 4 shows the nasal dam 107 and air chamber 103 fully engaged. The nasal dam 107 is prevented from moving along the X or Z axis by the slide which interferes with that motion due to the wedge present in the X-Z plane for Z axis motions and the length of the slide along the Y axis for X axis motion. Section A-A shows a cross section of the Air Chamber dove tail slide and Nasal Base slide opening.

Figure 2C:
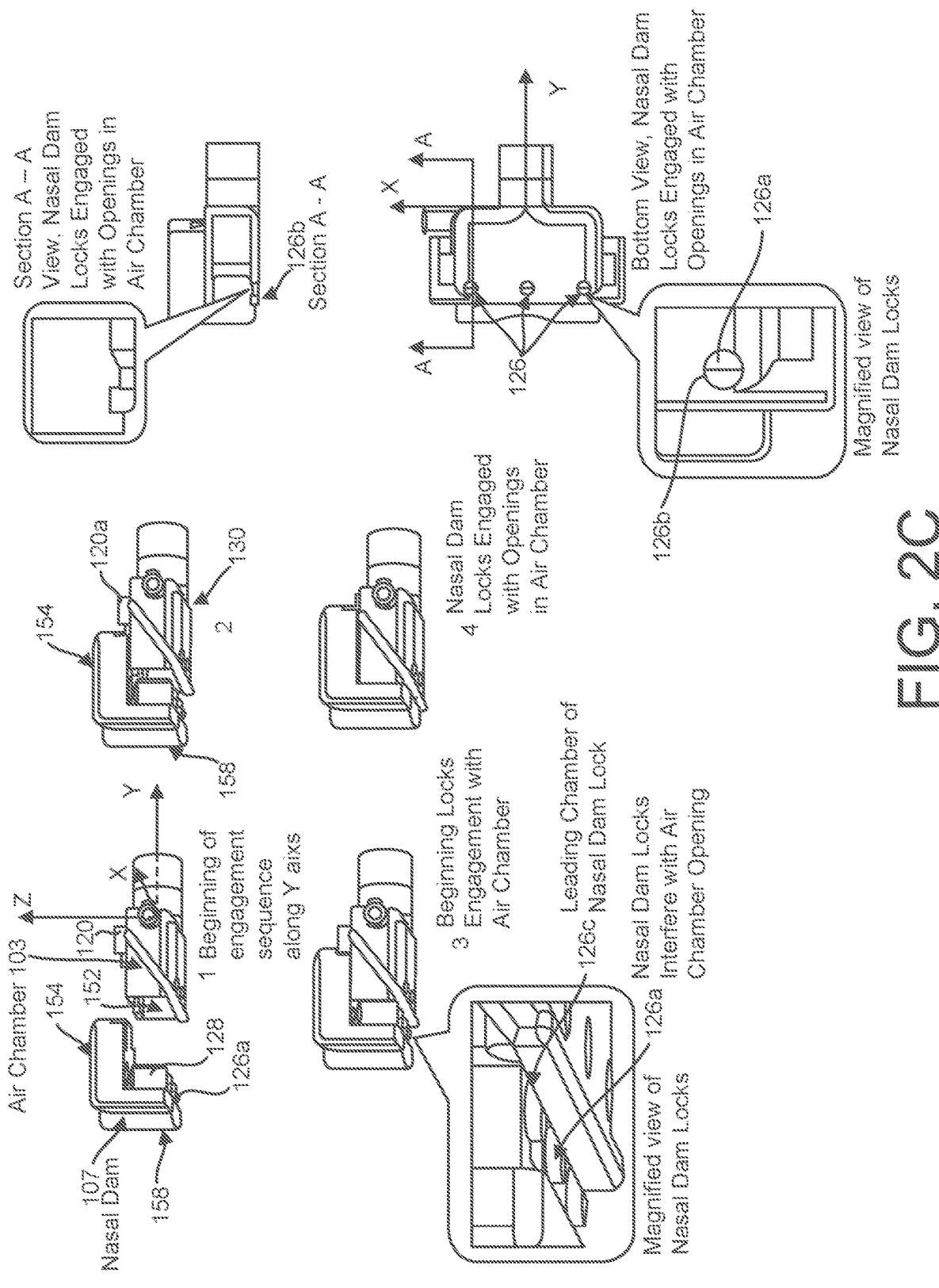
FIG. 2C further illustrates a step sequence for engaging the nasal dam with the air chamber to achieve an exemplary nasal respiratory apparatus.

The Nasal Dam to Air Chamber engagement sequence as it moves along the Y axis is illustrated in FIG. 2C with the nasal dam locks 126 being highlighted. Step 1 shows the beginning location of the nasal dam 107 relative to the Air chamber 103. Step 2 shows the nasal dam 107 moving towards the Air chamber 103 along the Y axis. Step 3 shows the leading chamfer 126c of the nasal dam lock projections 126a almost engaged with rear opening 152 of the Air chamber 103. Note the lock projections 126a interfere with the opening, but due to the nasal dam 107 material compressibility, continue motion along the Y axis is possible due to a leading chamfer 126c and lock compression of the Nasal Dam Lock projections 126a along the Z axis, temporarily removing the interference. Step 4 shows the nasal dam 107 and air chamber 103 fully engaged. The openings 126b in the air chamber 103 allow the nasal dam lock projections 126a to decompress along the Z axis. Once decompressed, they are contained in that location along the X-Y plane and prevent motion along the Y axis do to the Nasal Dam Lock—Air Chamber interference. A cross section of the Nasal Dam Lock projection 126 and Air Chamber Opening 126b is shown in Section A-A.

An alternate Nasal Dam to Air Chamber engagement approach from a top, side and bottom view is illustrated in FIG. 3. Posts 320a parallel to the Z axis replace the dovetails on the Air Chamber and Post holes 320b parallel to the Z axis replace the corresponding dove tail slots in the Nasal dam 107. Other elements of the device remain the same, including nasal dam locks as desired. The engagement sequence steps are described as follows:

Step 1 is to slide the Air Chamber plug portion of the nasal dam 107 along the +Y direction and enter the back of the air chamber 103

Step 2 is to lift the front of the nasal dam 107 so that it clears the posts on the Air chamber 103 as the nasal dam 107 is engaging with the Air chamber 103 by continuing to move along the +Y axis until seated into the Air chamber 103

Step 3 is to force the Post hole of the Nasal Dam over the Posts projecting along the Z axis from the X-Y top surface of the Air chamber 103 until the bottom of the Nasal dam X-Y surface is coincident with the Top Air chamber X-Y surface.

At this point the Nasal dam 107 is fully engaged and secured to the Air chamber 103. Although illustrated as being cylindrical posts, the posts can have effectively any cross section/shape in the X-Y plane and extend in the Z direction. Also, multiple posts can be replaced by a single post.

In addition to the Air Chamber as described above, various other configurations of the Air Chamber are possible, as described below, and may be modified to include the engagement features of the Nasal Dam and Air Chamber as described above. The nasal respiratory device described herein may incorporate any of the strap features described and claims in PCT/US19/68231, filed Dec. 23, 2019, and described below and the entirety of which is incorporated by reference as if fully set forth herein.

A coordinate system is used in explaining various embodiments. A right-handed X, Y, Z-axis Cartesian Coordinate system is illustrated in and referred to with respect to the features illustrated in FIGS. 4 and 5. As illustrated, the device has a gas connection port 401 parallel to the Y-axis, although the port could be parallel to the X or Z-axis. In certain circumstances, the Y-axis configuration may be advantageous over the Z-axis configuration for patient access for different types of procedures in that it can be used with the patient in a supine position (laying on the back) or lateral position with the patient lying on the left or right side.

Figure 4:
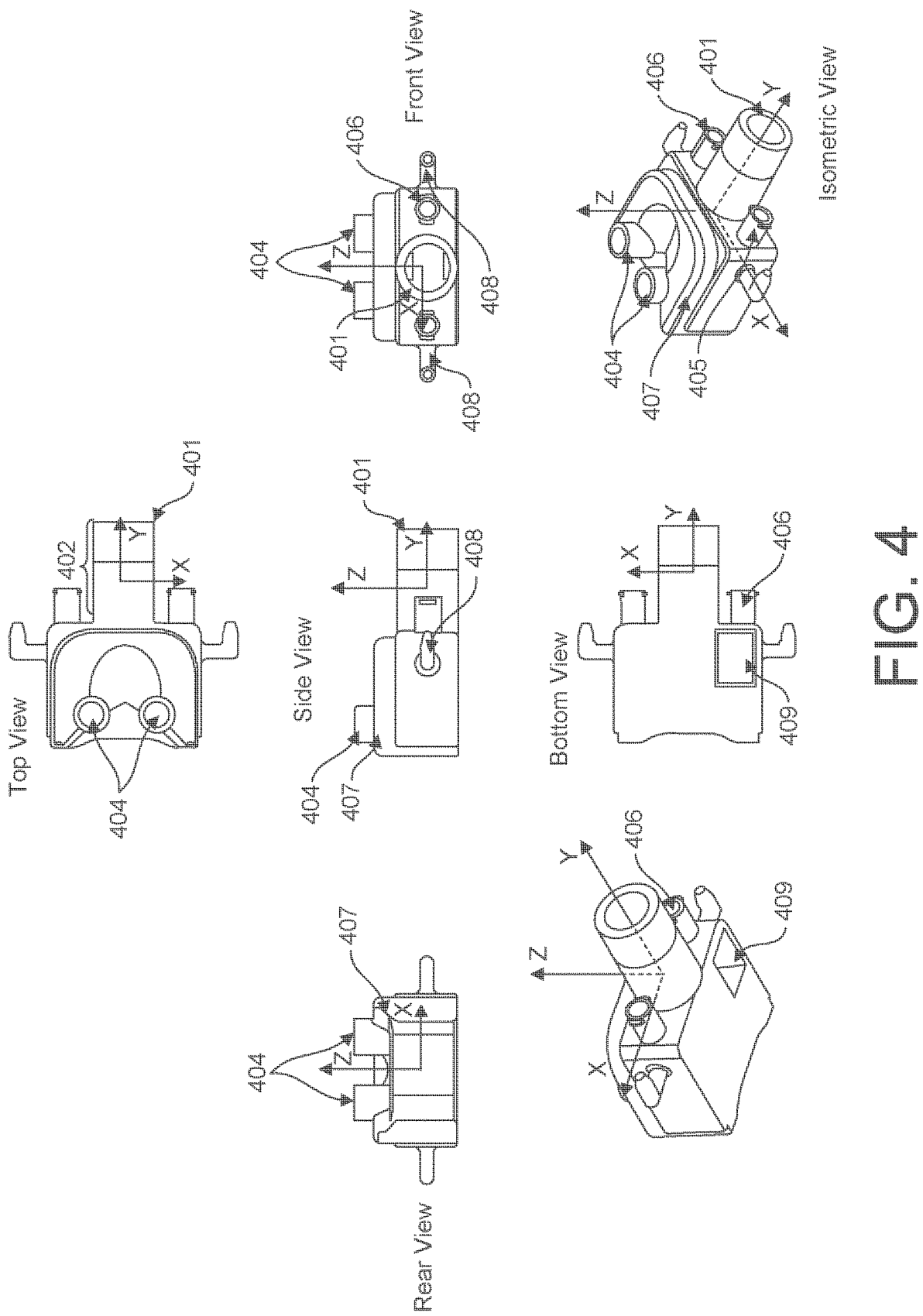
FIG. 4 illustrates a nasal respiratory apparatus related to principles described herein.

Elements of the nasal respiratory apparatus configuration with the gas connection port 401 parallel to the Y-axis are illustrated in FIG. 4. Referring to FIG. 4, gas connection port 401 provides interface with standard $O_2$ source, anesthesia machine, hyper-inflation bag, high-flow source or ventilator 8.5 mm, 11.5 mm, 15 mm or 22 mm conical connectors as defined by ISO 5356 or current equivalent standard. Other connector interfaces are possible. This port 401 is designed to fit male or female connectors. A male connection interface is shown on this illustration. Note the gas connection port or gas port connection 401 can be located in either the plus or minus direction in an orientation with its axis parallel to the X, Y or Z-axis.

Gas supply tube 402 is a conduit containing and allowing for the flow of gas between the gas connection port 401 and air chamber 403. The gas supply tube 402 can either be rigid or expandable. Being expandable will accommodate for different size heads and allow the tubing to expand and retract as patients move head up and down, side to side, or rotate. Air chamber 403 provides the structural and gas flow interface between the gas supply tube 402, at least one nares port(s) 404 and the end tidal sampling port 405. The one or two nares ports 404 provide the mechanical and gas flow interface between the patient's nares and the nasal respiratory apparatus.

The nasal end tidal sample port 405 is parallel to the X-axis and is an optional interface allowing for sampling of end tidal $CO_2$, end tidal $O_2$, or other nasally exhaled gas of interest via by a sampling device (not shown) such, etc. such as a Capnography Sensor, an oxygen sensor, or gas analyzer. The port exterior is a standard luer lock connector that interfaces with a sampling line (not shown) per ISO 80396-7: 2016(E) or current equivalent. A male or female connector can be implemented, a female interface is shown in the illustration. Alternate interfaces can also exist. The end tidal port 405 can be on the plus or minus X-axis side of the air chamber. The end tidal port being along the X, Y or Z-axis and on the +/−X side or +/−Z side and +Y side is also possible. The nasal and oral end tidal sample ports 405/406 can be connected individually to a sample line of a gas monitoring device (not shown), or can both be connected to the same gas sample line via a Y flow connector (not shown).

The oral end tidal sample port 406 parallel to the Y-axis is an interface allowing for sampling composition or levels of the oral end tidal $CO_2$, end Tidal $O_2$, etc. exhaled orally by a sampling device (not shown) such as a Capnography Sensor, an oxygen sensor, or gas analyzer. The port exterior is a standard luer lock connector that interfaces with a sampling line (not shown) per ISO 80396-7: 2016(E) or current equivalent. A male or female connector can be implemented; a female interface is shown for purposes of illustration. Alternate interfaces can also exist. The end tidal sample port 406 can be on the plus or minus X or Z-axis side of the air chamber 403. The nasal and oral end tidal sample ports 405/406 can be connected individually to the sample line of a gas monitoring device (not shown), or can both be connected to the same gas sample line via a Y flow connector (not shown).

A nasal dam 407 may surround the nares ports 404 and interfaces with the soft tissue of the nasal base, providing a pressure seal in order to contain airflow between the nasal pharynx and the nasal respiratory apparatus.

Head strap connectors 408 provide mechanical tie points 410 between the nasal respiratory apparatus and a head strap (not shown) that secures the nasal respiratory apparatus to the patient's head. An oral ventilation scoop 409 may be located below the air chamber 403, near the mouth of the patient. The scoop 409 may be substantially isolated from the air chamber 403 from a gas pressure and flow perspective. The scoop 409 may be common to the oral end tidal sample port 406. In such configuration, when gas is expelled from the mouth, a portion flows into the oral ventilation scoop 409 to the oral end tidal sample port 406 and onto a gas monitoring device (not shown) if it is connected by a sample line (not shown).

During the inhalation portion of the breathing cycle, pressurized gases (i.e. Oxygen ($O_2$), air anesthetic agents etc.) are provided by a source (wall $O_2$ supply, bottled $O_2$ supply, ventilation machine, anesthesia machine continuous positive airway pressure (CPAP) machine, bilevel positive airway pressure (BiPAP) or another device). It enters the nasal respiratory apparatus via the gas connection port 401, travels through the gas supply tube 402 and the air chamber 403 finally flowing out the nares port(s) 404. gas leaves the nares port(s) 404, traveling through the patient's nasal pharynx and eventually reaches the patient's lungs, where it is absorbed into the blood stream. During the exhalation portion of the breathing cycle, waste $CO_2$ and unabsorbed gases are expelled from the lungs by pressure created by the diaphragm and ventilated in the opposite direction out of the lungs, thorough the nares port(s) 404, traveling through the air chamber 403, the gas supply tube 402 and out the gas connection port 401. A small amount of ventilated gas (i.e., carbon dioxide ($CO_2$), oxygen, anesthetic gases, etc.) can be sampled out of the nasal end tidal sample port 405/406 by a monitoring device. If the patient exhales orally, gas from the mouth enters the oral ventilation scoop 409 and enters the oral end tidal sample port 406. Both the nasal and oral end tidal sample ports 405/406 are connected either separately, or through a Y connector (not shown) to a common sample line attached to a gas monitoring device.

Figure 5:
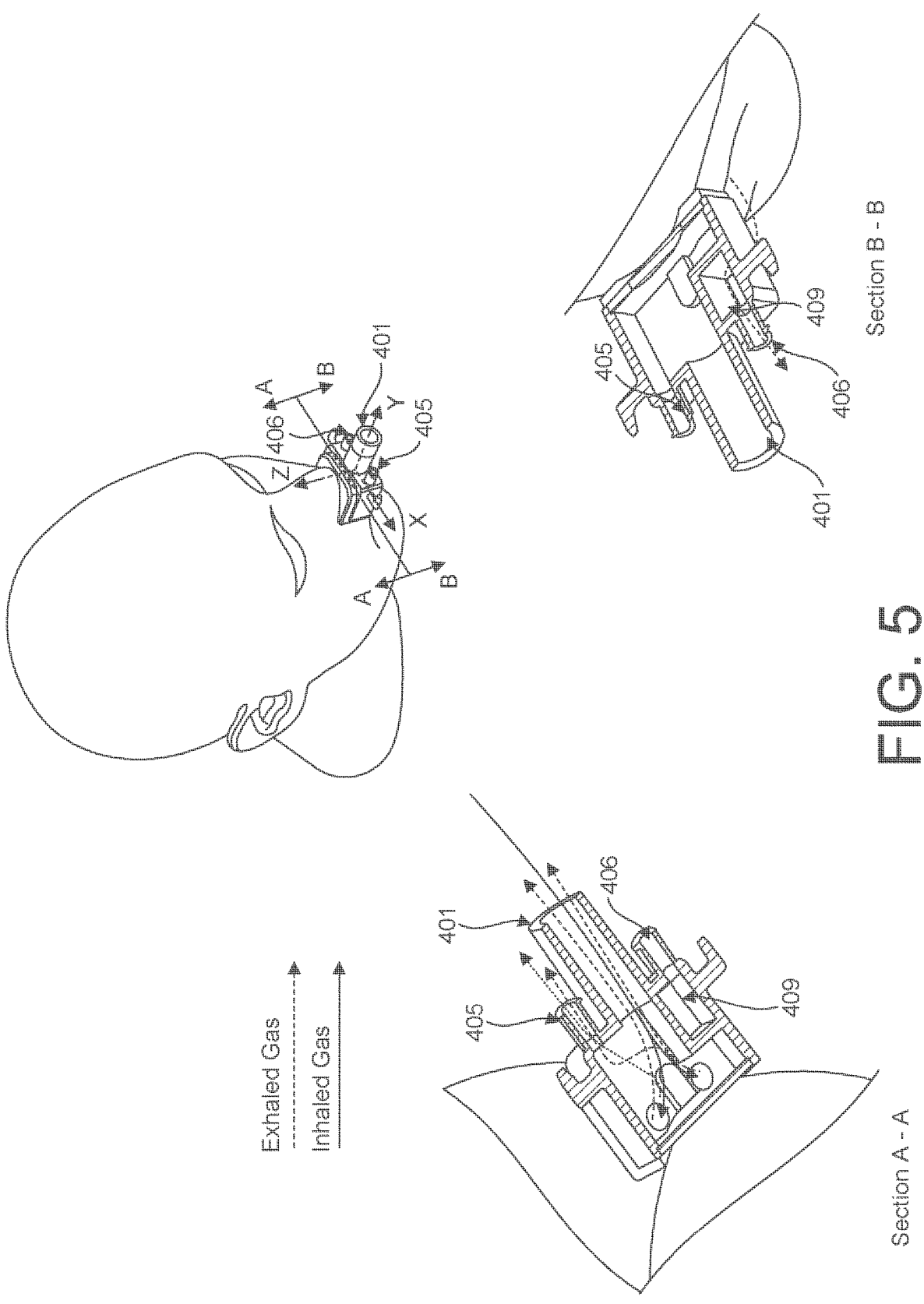
FIG. 5 illustrates cross-sectional views of illustrates a nasal respiratory apparatus related to principles described herein with nasal and oral end tidal sampling ports.
Figure 6:
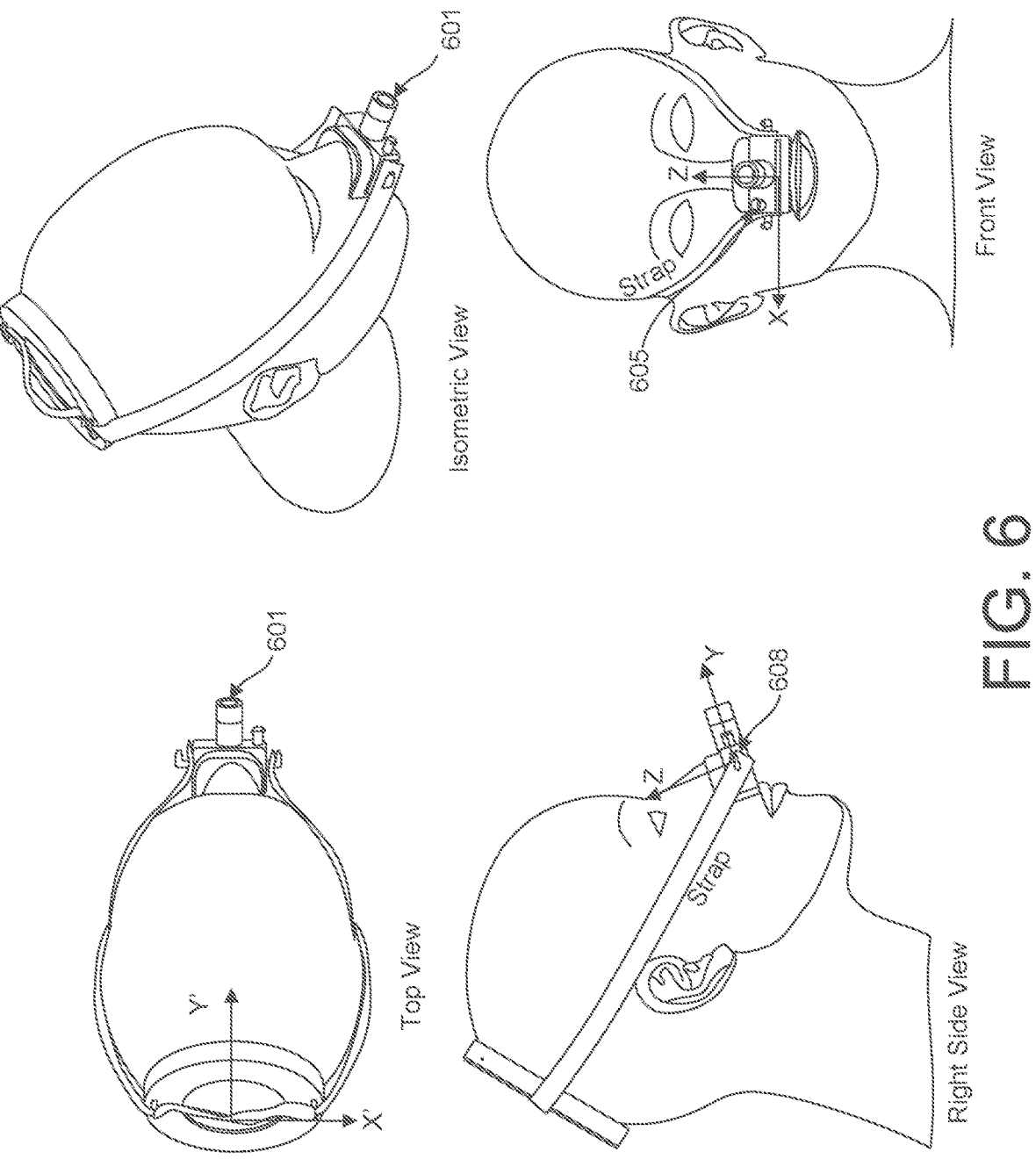
FIG. 6 illustrates a nasal respiratory apparatus with head strap related to principles described herein.

The present embodiment allows for sampling of $CO_2$ or other gases that are exhaled nasally and or orally. FIG. 5 shows cross-sections A-A and B-B of the nasal respiratory apparatus device. As illustrated, the gas connection port 401, nares port(s) 404 and nasal end tidal sample port 405 are all common to the air chamber 403. The oral ventilation scoop 409 provides an opening below the air chamber 403, near the mouth opening, and the flow path is substantially isolated from the air chamber 403, but is common to the oral end tidal sampling port 406. During the inspiratory portion of a breathing cycle, external gas enters the gas connection port 401 into the air chamber 403, where it then leaves the air chamber 403 through the nares port(s) 404, entering the nasal pharynx and ultimately into the lungs. This phase is illustrated by FIG. 5, Section A-A. During the expiratory phase of the breathing cycle, exhaled gasses can leave the lungs nasally, orally or both. If the gas leaves nasally, as illustrated in FIG. 5, Section A-A, gas flows out the gas connection port 401 and a portion also flows out the nasal end tidal sample port 405, which may be attached to a gas monitoring device (not shown). Alternatively, the nasal end tidal sample port 405 may be plugged or capped (not shown). If the gas leaves orally as illustrated in FIG. 5, Section B-B, gas flows out the mouth and a portion also flows into the oral ventilation scoop 409 and into the oral end tidal sample port 406, which may be attached to a gas monitoring device (not shown). Alternatively, the oral end tidal sample port may be plugged or capped (not shown). It is possible that gases are exhaled from both the nose and the mouth, in which case they could be sampled via the associated nasal and oral end tidal sample ports 405/406.

Figure 7:
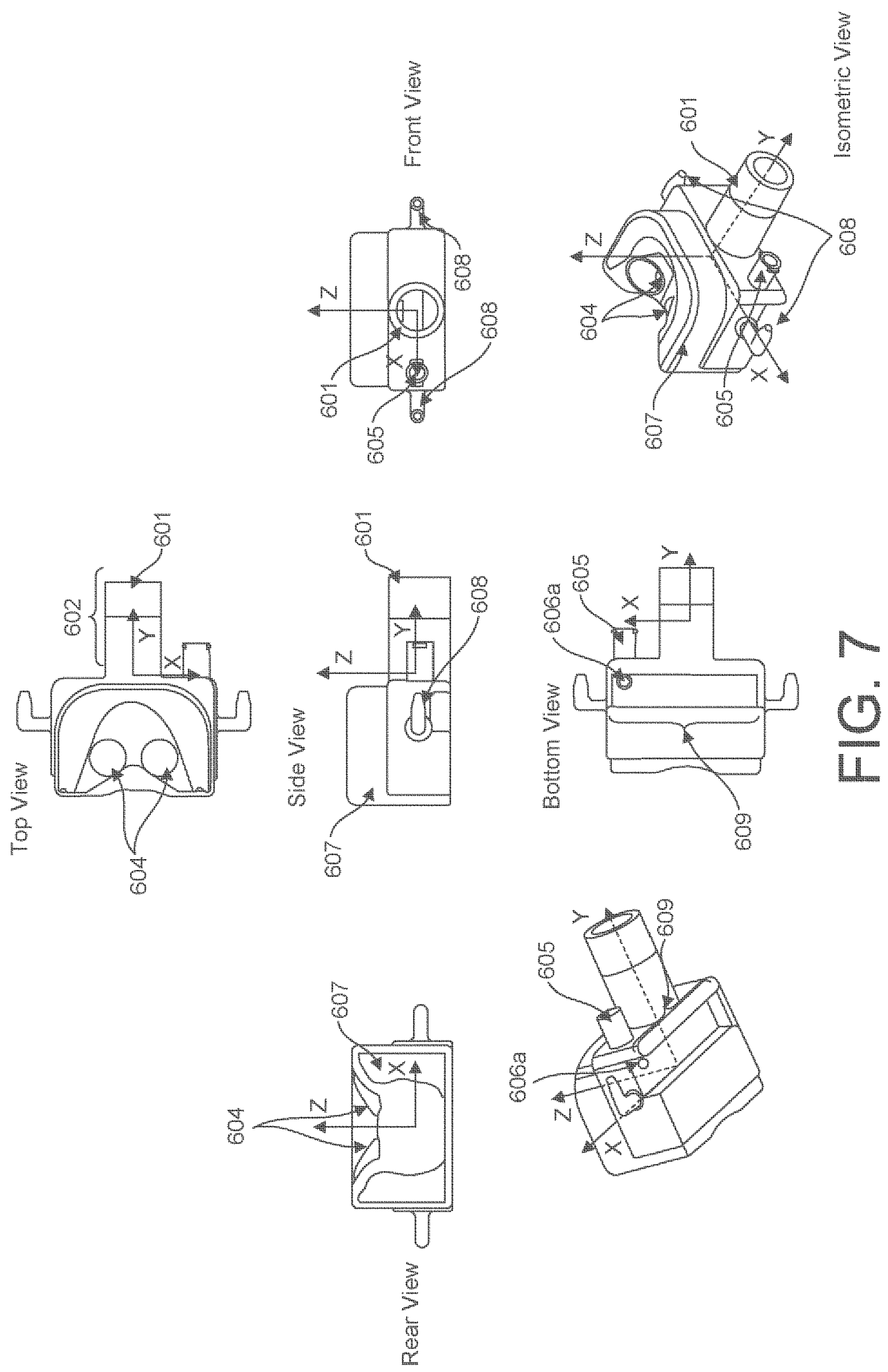
FIG. 7 illustrates a nasal respiratory apparatus related to principles described herein with nasal and oral end tidal sampling ports
Figure 8:
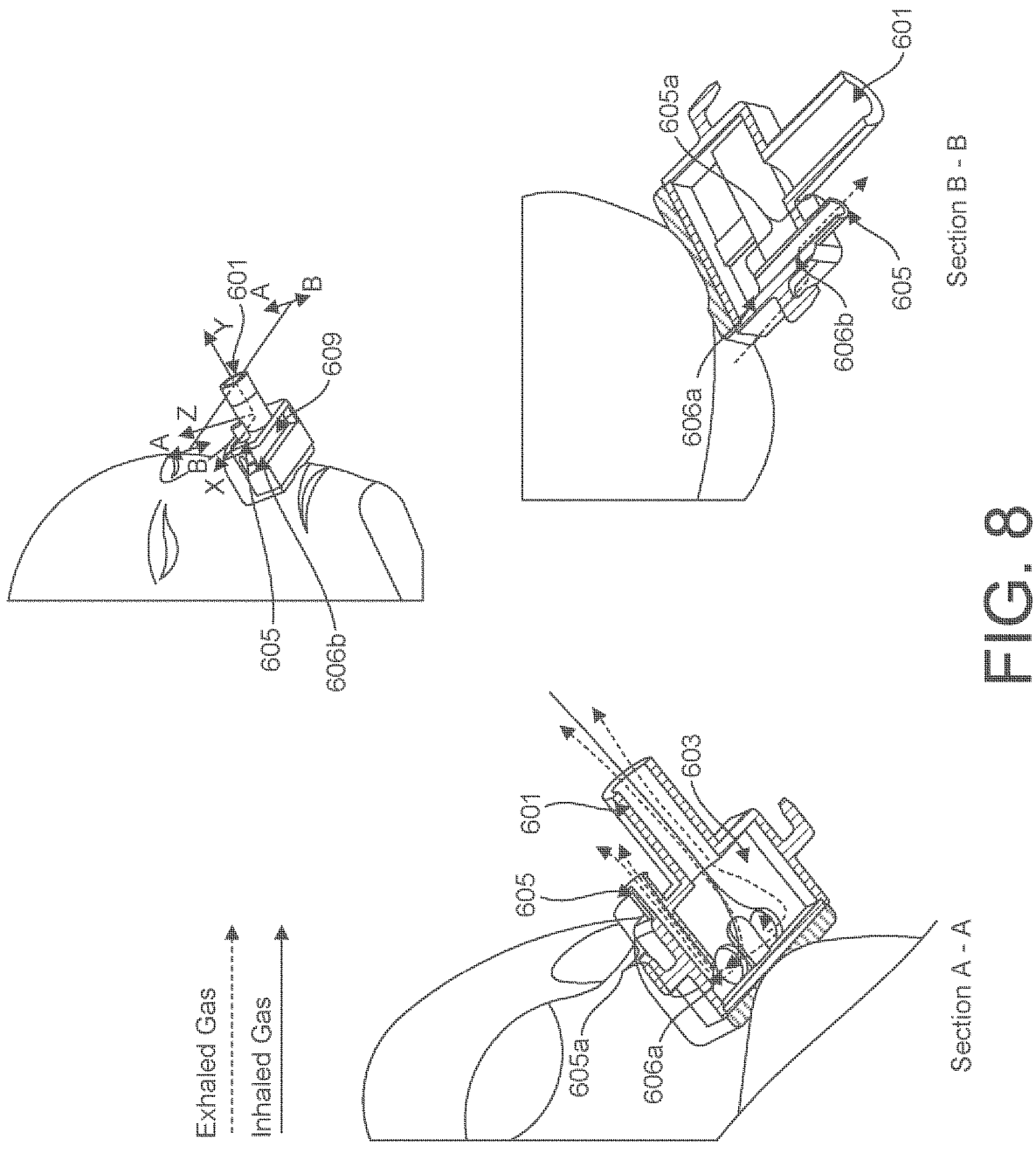
FIG. 8 illustrates cross-sectional view of a nasal respiratory apparatus related to principles described herein with nasal and oral end tidal sampling ports with combined nasal/oral end tidal sample port.

A right-handed X, Y, Z-axis Cartesian Coordinate system is illustrated in and referred to with respect to the features illustrated in FIGS. 7 and 8. An embodiment of the nasal respiratory apparatus may be configured to have a gas connection port parallel to the Y-axis, although the port could be parallel to the X or Z-axis, FIG. 7. This configuration may be advantageous over the Z-axis configuration for patient access for different types of procedures in that it can be used with the patient in a supine position (laying on the back) or lateral position with the patient lying on the left or right side.

Elements of the nasal respiratory apparatus configuration with the gas connection port 601 parallel to the Z-axis are illustrated in FIG. 7. During the inhalation portion of the breathing cycle, pressurized gases (i.e., Oxygen ($O_2$), air anesthetic agents etc. are provided by a source (wall $O_2$ supply, bottled $O_2$ supply, ventilation machine, anesthesia machine continuous positive airway pressure (CPAP) machine, bilevel positive airway pressure (BiPAP) machine or another device)). Administered gas enters the nasal respiratory apparatus via the gas connection port 601, travels through the gas supply tube 602 and the air chamber 603, finally flowing out at least one nares port 604. gas leaves the nares port(s) 604, traveling through the patient's nasal pharynx and eventually reaches the patient's lungs, where it is absorbed into the blood stream. During the exhalation portion of the breathing cycle, waste $CO_2$ and unabsorbed gases are expelled from the lungs by pressure created by the diaphragm and ventilated in the opposite direction out of the lungs, through the nares port(s), traveling through the air chamber 603, the gas supply tube 602 and out the gas connection port 601. A small amount of ventilated gas (i.e., carbon dioxide ($CO_2$), oxygen, anesthetic gases, etc.) can be sampled out of the single nasal/oral end tidal sample port 605 by a monitoring device (not shown). If the patient exhales orally, gas from the mouth enters the oral ventilation scoop 609 and enters the nasal/oral end tidal sample port 605. The combined nasal and oral end tidal sample port 605 is connected to a sample line (not shown) attached to a gas monitoring device (not shown). Alternatively, if exhaled gas is not to be sample, one or both of the end tidal sample ports may be plugged or capped.

Gas connection port 601 provides interface with standard $O_2$ source, anesthesia machine, hyper-inflation bag, high-flow source or ventilator 8.5 mm, 11.5 mm, 15 mm or 22 mm conical connectors as defined by ISO 5356 or current equivalent standard. Other connector interfaces are possible. This port is designed to fit male or female connectors. A male connection interface is shown on this illustration. gas connection port 601 can be located in either the plus or minus direction in an orientation with its axis parallel to the X, Y or Z-axis. gas supply tube 602 is a conduit containing and allowing for the flow of gas between the gas connection port 601 and the air chamber 603. The gas supply tube 602 can either be rigid or expandable. Being expandable will accommodate for different size heads and allow the tubing to expand and retract as patients move head up and down, side to side, or rotate. Air chamber 603 provides a structural and gas flow interface between the gas supply tube 602, the nares port(s) 604 and the end tidal sampling port 605. One or two nares ports 604 provide the mechanical and gas flow interface between the patient's nares and the nasal respiratory apparatus.

The nasal/oral end tidal sample port 605 parallel to the Y-axis is an optional interface allowing for sampling of the end tidal $CO_2$, end tidal $O_2$, etc. level from nasal exhalation by a sampling device such as a Capnography Sensor, an oxygen sensor, or gas analyzer. The port exterior is a standard luer lock connector that interfaces with a sampling line per ISO 80396-7: 2016(E) or current equivalent. A male or female connector can be implemented, a female interface is shown in the illustration. Alternate interfaces can also exist. Note the end tidal sample port 605 can be on the plus or minus X-axis side of the air chamber. The end tidal sample port 605 can be on the plus or minus X or Z-axis side of the air chamber.

An end tidal sample channel 605a has an opening into the air chamber 603 via a nasal opening 606a to the end tidal sample channel 605a and an oral ventilation scoop 609 via an oral opening 606b to the end tidal sample channel 605a where it then terminates at the port opening. $CO_2$ exhaled nasally into the air chamber 603 enters the end tidal sample channel 605a via the nasal opening 606a to the end tidal sample channel 605a. $CO_2$ exhaled orally into the oral ventilation scoop 609 enters the end tidal sample channel 605a via the oral ventilation opening 606b to the end tidal sample channel 605a. A nasal dam 607 may surrounds the nares ports 604 and interfaces with the soft tissue of the patient's nasal base, providing a pressure seal in order to contain airflow between the patient's nasal pharynx and the nasal respiratory apparatus. Head strap connectors 608 provide mechanical tie points between the nasal respiratory apparatus and a head strap that secures the nasal respiratory apparatus to the patient's head.

An oral ventilation scoop 609 is located below the air chamber 603, near the mouth. When gas is expelled from the mouth, a portion flows into the oral ventilation scoop 609 to the oral opening 606b to the end tidal sample channel 605a, out the gas connection port 601 and onto a gas monitoring device (not shown) if it is connected by a sample line (sample line).

The present configuration allows for sampling of $CO_2$ or other gases that are exhaled nasally and or orally. FIG. 8 shows cross-sections A-A and B-B of the nasal respiratory apparatus device. The gas connection port 601, nares ports 604 and nasal opening 606a to the nasal/oral end tidal sample port 605 are all common to the air chamber 603. The oral ventilation scoop 609 provides an opening below the air chamber 603, near the mouth opening, and the flow path is common to the nasal/oral end tidal sampling port 605 by an oral opening 606b to the end tidal sample port 605 closer to an interface with the end tidal sample channel 605a with a Luer connector. During the inspiratory portion of a breathing cycle, external gas enters the gas connection port 601 into the air chamber 603, where it then leaves the air chamber 603 through the nares port(s), entering the patient's nasal pharynx and ultimately into the lungs. This phase is illustrated by FIG. 8, Section A-A. During the expiratory phase of the breathing cycle, exhaled gasses can leave the lungs nasally, orally or both. If the gas leaves nasally as illustrated in FIG. 8, Section A-A, gas flows out the gas connection port 601 and a portion also flows out the nasal opening 606a to the end tidal sample channel 605a then out the gas connection port 601 if it is attached to a gas monitoring device (not shown). If the gas leaves orally as illustrated in FIG. 8, Section B-B, gas flows out the mouth and a portion also flows into the oral ventilation scoop 609 and into the oral opening 606b to the end tidal sample channel 605a and out the nasal/oral end tidal sample port 605 if it is attached to a gas monitoring device (not shown).

Figure 9:
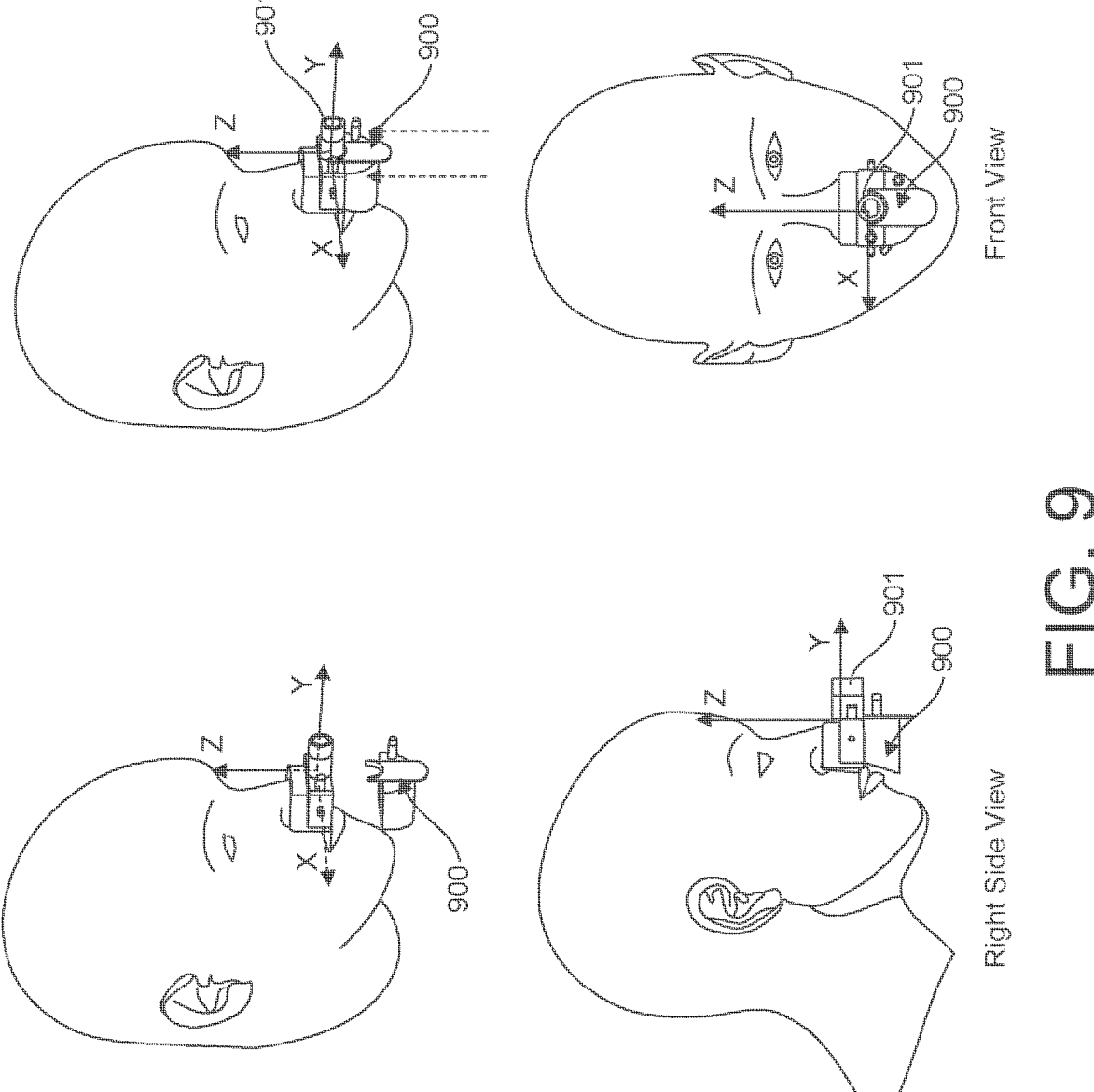
FIG. 9 illustrates a nasal respiratory apparatus related to principles described herein with nasal and oral end tidal sampling ports and end tidal ventilation scoop (gas connection port Parallel to Y-axis with Combined nasal and oral end tidal sample port).
Figure 10:
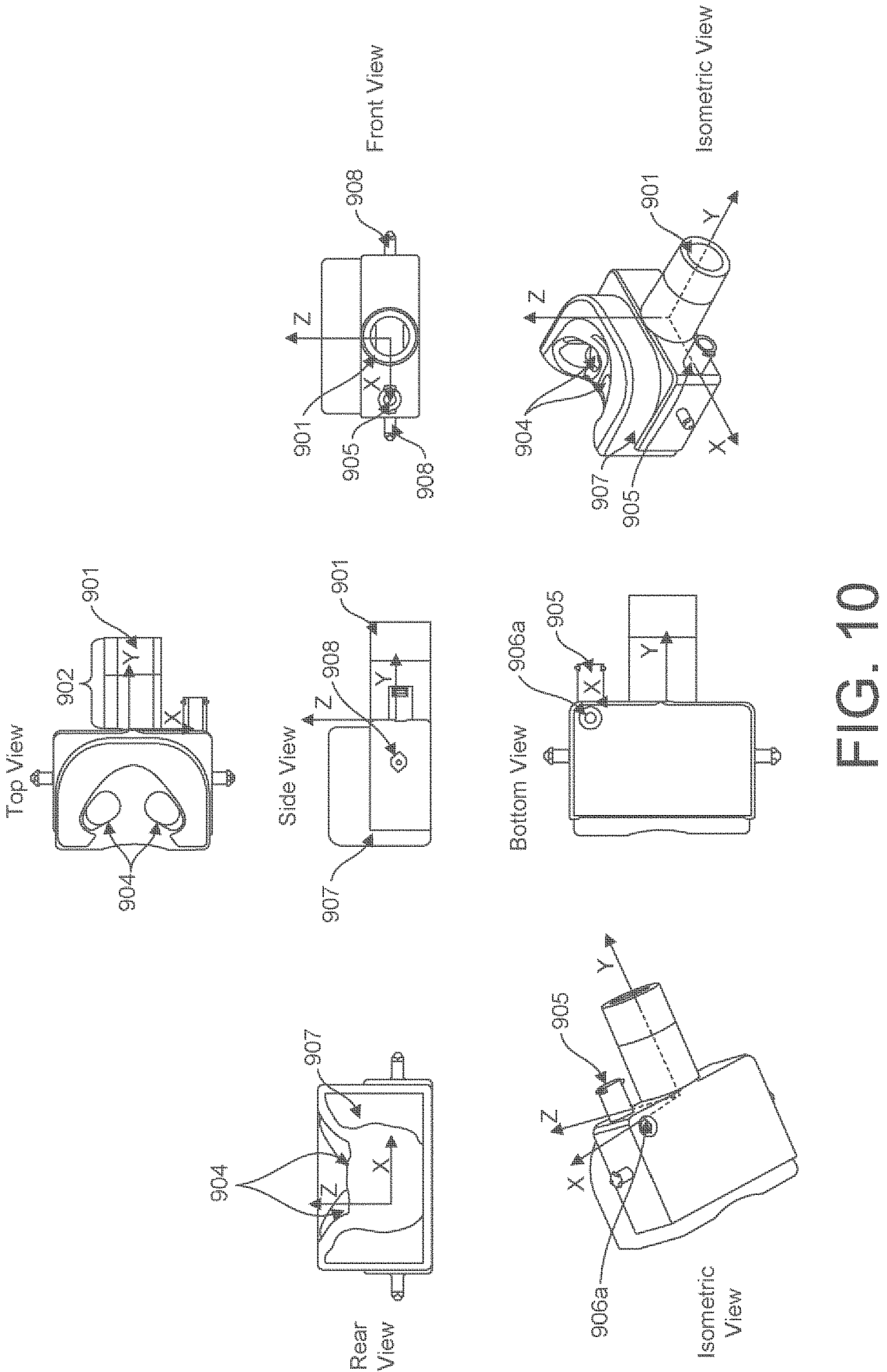
FIG. 10 illustrates a nasal respiratory apparatus related to principles described herein with nasal and oral end tidal sampling ports (gas connection port Parallel to Z-axis).

Referring to FIGS. 9 and 10, a system incorporating nasal respiratory apparatus according to principles described herein includes a gas connection port parallel to the Y-axis, FIG. 9, although the port could be parallel to the X or Z-axis. The illustrated configuration may be advantageous over the Z-axis configuration for patient access for different types of procedures in that it can be used with the patient in a supine position (laying on the back) or lateral position with the patient lying on the left or right side. A ventilation scoop may be separate from the nasal respiratory apparatus in the system shown. The ventilation scoop may clip onto the gas connection port, as illustrated in FIG. 9. As described herein, such a clipping or modular style connection between an accessory, such as the ventilation scoop, and the gas connection port, can be used for accessories other than or in addition to a ventilation scoop.

Elements of the nasal respiratory apparatus) configuration with a gas connection port 901 parallel to the Y-axis are illustrated in FIG. 10.

Gas connection port 901 provides interface with standard $O_2$ source, anesthesia machine, hyper-inflation bag, high-flow source or ventilator 8.5 mm, 11.5 mm, 15 mm or 22 mm conical connectors as defined by ISO 5356 or current equivalent standard. Other connector interfaces are possible as well as other gas supplies, including continuous positive airway pressure (CPAP) machine and/or bilevel positive airway pressure (BiPAP) machine or another device. The gas connection port 901 is designed to fit male or female connectors. A male connection interface is shown on this illustration. The gas connection port 901 can be located in either the plus or minus direction in an orientation with its axis parallel to the X, Y or Z-axis.

A gas supply tube 902 is a conduit containing and allowing for the flow of gas between the gas connection port 901 and an air chamber 903. The gas supply tube can either be rigid or expandable. Being expandable will accommodate for different size heads and allow the tubing to expand and retract as patients move head up and down, side to side, or rotate. Air chamber 903 provides a structural and gas flow interface between the gas supply tube 902, at least one nares port 904 and an end tidal sample port 905. One or two nares ports 904 provide the mechanical and gas flow interface between a patient's nares and the nasal respiratory apparatus. A nasal/oral end tidal sample port 905 parallel to the Y-axis is an optional interface allowing for sampling of the end tidal $CO_2$, end tidal $O_2$, or other oral exhaled gas the level or composition of which is of interest, by a sampling device (not shown) such as a Capnography Sensor, an oxygen sensor, or gas analyzer. The nasal/oral end tidal sample port may be a described in relation to other embodiments of the nasal respiratory apparatus describe herein. A port exterior may be a standard luer lock connector that interfaces with a sampling line per ISO 80396-7: 2016(E) or current equivalent. A male or female connector can be implemented, a female interface is shown in the illustration. Alternate interfaces can also exist. The end tidal sample port 905 can be on the plus or minus X-axis side of the air chamber. The end tidal sample port can be on the plus or minus X or Z-axis side of the air chamber 903.

The end tidal sample channel 905a has an opening into the air chamber 903 via a nasal opening 906a to the end tidal sample channel 905a and an oral ventilation scoop 909 via an oral opening 906b to the end tidal sample channel 905a where it then terminates at the opening of the gas connection port 901. $CO_2$ exhaled nasally into the air chamber 903 enters the end tidal sample channel 905a via the nasal opening 906a to the end tidal sample channel 905a. $CO_2$ exhaled orally into the oral ventilation scoop and supplemental $O_2$ port ventilation chamber 909 enters the end tidal sample channel 905a via the oral ventilation chamber 909 to oral opening of the ventilation scoop 906b.

A nasal dam 907 may surround the nares ports and interfaces with the soft tissue of the patient's nasal base, providing a pressure seal in order to contain airflow between the patient's nasal pharynx and the nasal respiratory apparatus. Head strap connectors 908 provide mechanical tie points between the nasal respiratory apparatus and a head strap (not shown) that secures the nasal respiratory apparatus to the patient's head.

During the inhalation portion of the breathing cycle, pressurized gases (i.e., Oxygen ($O_2$)), air anesthetic agents etc.) are provided by a source (wall $O_2$ supply, bottled $O_2$ supply, ventilation machine, anesthesia machine continuous positive airway pressure (CPAP) machine, bilevel positive airway pressure (BiPAP) machine or another device). It enters the nasal respiratory apparatus via the gas connection port 901, travels through the gas supply tube 902 and the air chamber 903 finally flowing out the nares port(s). gas leaves the nares port(s), traveling through the patient's nasal pharynx and eventually reaches the patient's lungs, where it is absorbed into the blood stream. During the exhalation portion of the breathing cycle, waste $CO_2$ and unabsorbed gases are expelled from the lungs by pressure created by the diaphragm and ventilated in the opposite direction out of the lungs, thorough the nares port(s), traveling through the air chamber 903, the gas supply tube 902 and out the gas connection port 901. A small amount of ventilated gas (i.e., carbon dioxide $CO_2$, oxygen, anesthetic gases, etc.) can be sampled out of the single nasal/oral end tidal sample port 905 by a monitoring device (not shown). If the patient exhales orally, gas from the mouth enters the oral ventilation scoop 909 and enters the nasal/oral end tidal sample port 905. The combined nasal and oral end tidal sample port 905 may be connected to a sample line (not shown) attached to a gas monitoring device (not shown). Additionally, a supplemental $O_2$ port may be provided as part of the ventilation scoop 909 where the supply line from an $O_2$ source can be plugged into the $O_2$ port, providing gases orally.

Figure 11:
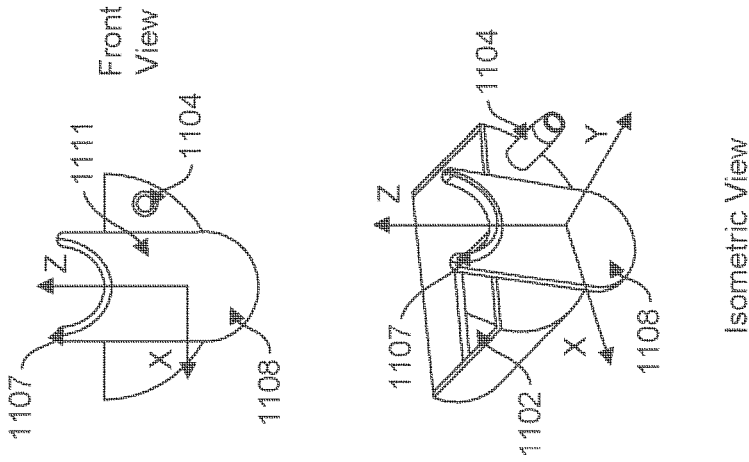
FIG. 11 illustrates a ventilation scoop and supplemental $O_2$ port related to principles described herein.
Figure 11:
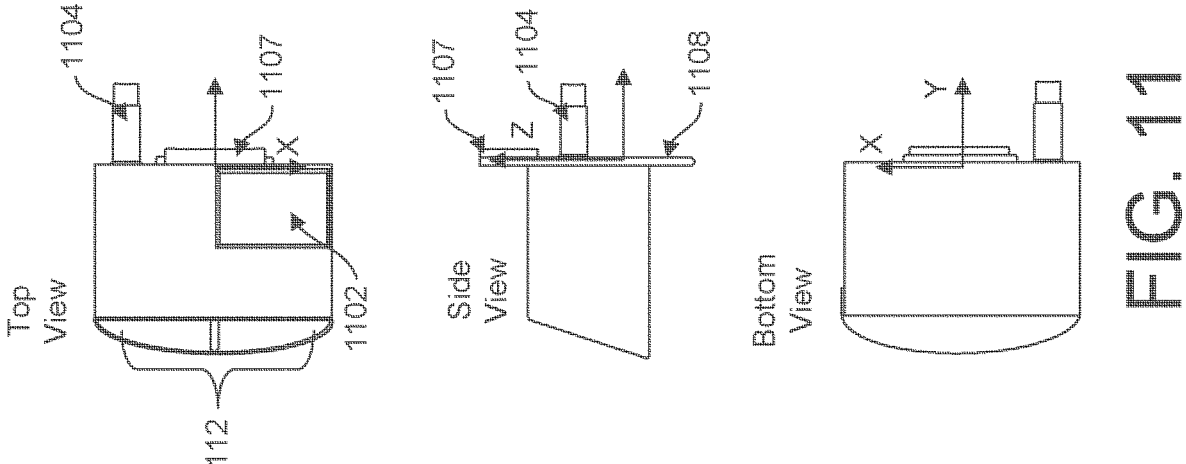
Figure 11:
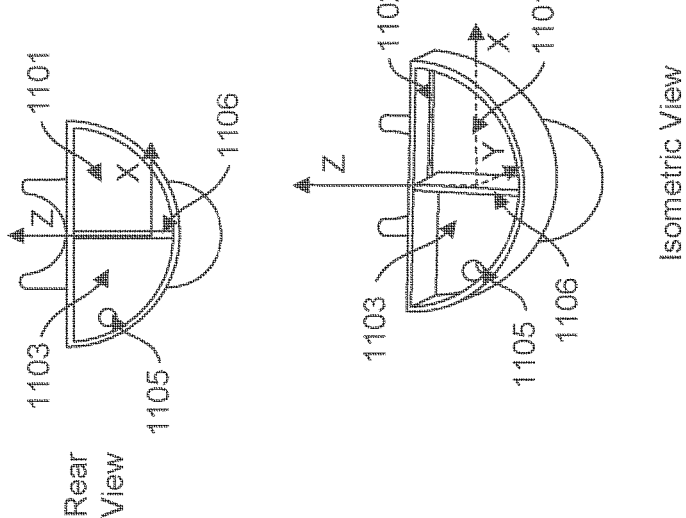

Another embodiment of the ventilation scoop and supplemental $O_2$ port 900 are illustrated in FIG. 11. ventilation scoop and supplemental $O_2$ port ventilations coop supplemental port 900 snaps onto a gas connection port 1101 of the nasal respiratory apparatus. The ventilation scoop and supplemental $O_2$ port illustrated in FIG. 11 has two chambers separated by a wall 1106 in order to minimize flow from the supplemental $O_2$ chamber 1103 to dilute exhaled gases flowing into the ventilation chamber 1150. The ventilation chamber 1150 opening is located near the patient's mouth and channels exhaled gases towards the oral opening 1113b to the end tidal sample channel 1105a of the nasal respiratory apparatus. The ventilation chamber to oral opening of the ventilation scoop 1151 and the oral opening of the nasal respiratory apparatus may be coincident. If the patient is breathing orally, fresh gas is provided via the supplemental $O_2$ chamber with the opening located near the patient's mouth.

The ventilation chamber 1150 has an opening near the patient's mouth and provides a channel to the oral opening 1113b to end tidal sample channel 1105a of the nasal respiratory device. The ventilation chamber to nasal respiratory apparatus 1100 oral opening 1102 is located on the chamber top wall 1110 of the ventilation chamber 1150. It is coincident with the oral opening 1113b of the nasal respiratory device 1100 and allows exhaled gas to enter the oral opening 1113b of the nasal respiratory device. The supplemental $O_2$ chamber 1103 has an opening near the patient's mouth and allows for flow from a supplemental $O_2$ port 1104 to the patient who is breathing orally. The supplemental $O_2$ port 1104 is located on the chamber front wall 1111 of the supplemental $O_2$ chamber 1103 and connects to the supply line (not shown) of an $O_2$ or air source.

The $O_2$ port opening to $O_2$ chamber 1115 allows for gas flow between the supplemental $O_2$ port 1104 and the supplemental $O_2$ chamber 1103. A chamber separation wall 1106 separates supplemental $O_2$ flow in the supplemental $O_2$ chamber and ventilation flow in the ventilation chamber 1150. This is intended to minimize dilution of the exhaled gases that are sampled via the nasal/oral end tidal port 1105 of the nasal respiratory device.

A nasal respiratory gas port clip 1107 secures the ventilation scoop and supplemental $O_2$ port 900 to the nasal respiratory apparatus 1100. This occurs when the gas port clip 1107 is forced onto the gas connection port 1101 of the nasal respiratory apparatus in the Z direction and opening of the clip separates in the X-Z plane. As the clip 1107 continues to move in the Z direction, the clip 1107 wraps around the gas connection port 1101 and is clipped to the port 1107, securing it. The chamber top wall 1110 is then coincident with the bottom surface of the nasal respiratory device, preventing rotation about the Y-axis.

A push-pull Tab 1108 allows the clinician to attach or detach the ventilation scoop and supplemental $O_2$ port 900 to/from the nasal respiratory apparatus 1100. This is accomplished by pushing with a force in the Z direction to attach and pulling with a force in the −Z direction to detach. The chamber outer wall 1109 separates the supplemental $O_2$ chamber 1103 and the ventilation chamber 1150 from the outside environment radially about the Y-axis in the −Z direction. The chamber top wall 1110 separates the supplemental $O_2$ chamber 1103 and ventilation chamber 1150 from the outside environment radially about the Y-axis in the Z direction. The exception is the ventilation chamber to nasal respiratory apparatus oral opening 1113b in the ventilation chamber 1150. The chamber front wall 1111 separates the supplemental $O_2$ chamber 1103 and ventilation chamber 1150 from the outside environment axially in the Y direction. Both the supplemental $O_2$ chamber 1103 and ventilation chamber 1150 are open to the outside environment axially in the Y direction, near the patient's mouth via chamber openings 1112.

Figure 12:
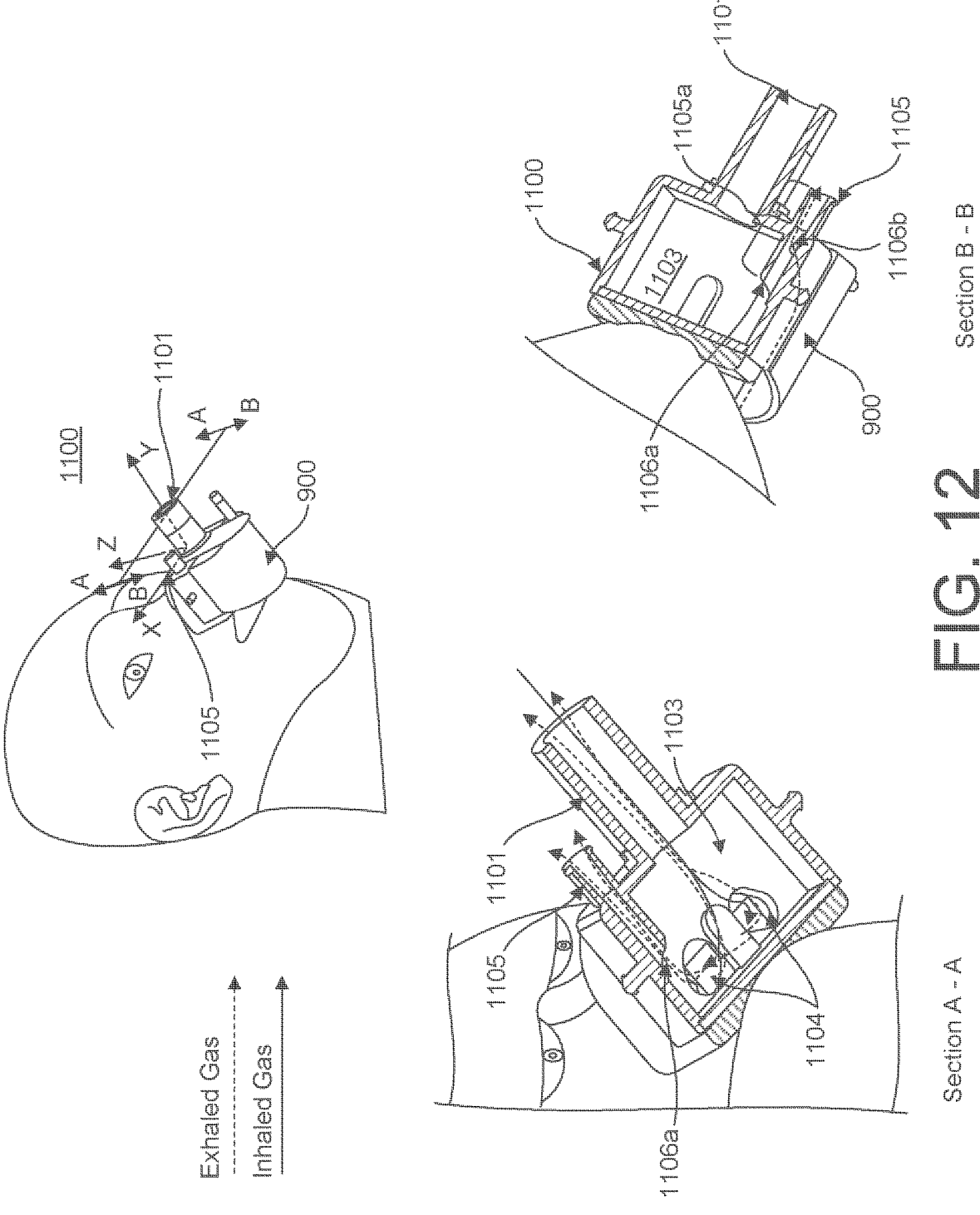
FIG. 12 are cross-sectional views illustrating a nasal respiratory apparatus with combined nasal/oral portend tidal sample port.

The present embodiment allows for sampling of $CO_2$ or other gases that are exhaled nasally and or orally. FIG. 12 shows cross-sections A-A and B-B of the nasal respiratory apparatus 1100. The gas connection port 1101, nares ports 1114 and nasal opening 1106a to the nasal/oral end tidal sample port 1105 are all common to the air chamber 1116. The ventilation scoop and supplemental $O_2$ port 900 routes exhalation to an opening below the air chamber 1116, near the mouth opening, and the flow path is common to the nasal/oral end tidal port 1105 by an oral opening 1113b to the end tidal sample port closer to an interface with a sample channel with a Luer connector. During the inspiratory portion of a breathing cycle, external gas enters the gas connection port 1101 into the air chamber 1116 where it then leaves the air chamber 1116 through the nares port 1114, entering the patient's nasal pharynx and ultimately into the lungs. This phase is illustrated by FIG. 12, Section A-A. During the expiratory phase of the breathing cycle, exhaled gasses can leave the lungs nasally, orally or both. If the gas leaves nasally as illustrated in FIG. 12, Section A-A, gas flows out the gas connection port 1101 and a portion also flows out the nasal opening 1104 to the end tidal sample channel then out the gas connection port 1101 if it is attached to a gas monitoring device. If the gas leaves orally as illustrated in FIG. 12, Section B-B, gas flows out the mouth and a portion also flows into the ventilation chamber 1150 of the ventilation scoop and supplemental $O_2$ port 900, out the ventilation chamber 1150 to nasal respiratory apparatus oral opening 1106b and into the oral opening 1113b of the end tidal sample channel. It then leaves the channel and out the nasal/oral end tidal port if it is attached to a gas monitoring device (not shown). If end tidal gasses are not to be monitored, the nasal and/or oral end tidal ports may be plugged or capped.

Figure 13:
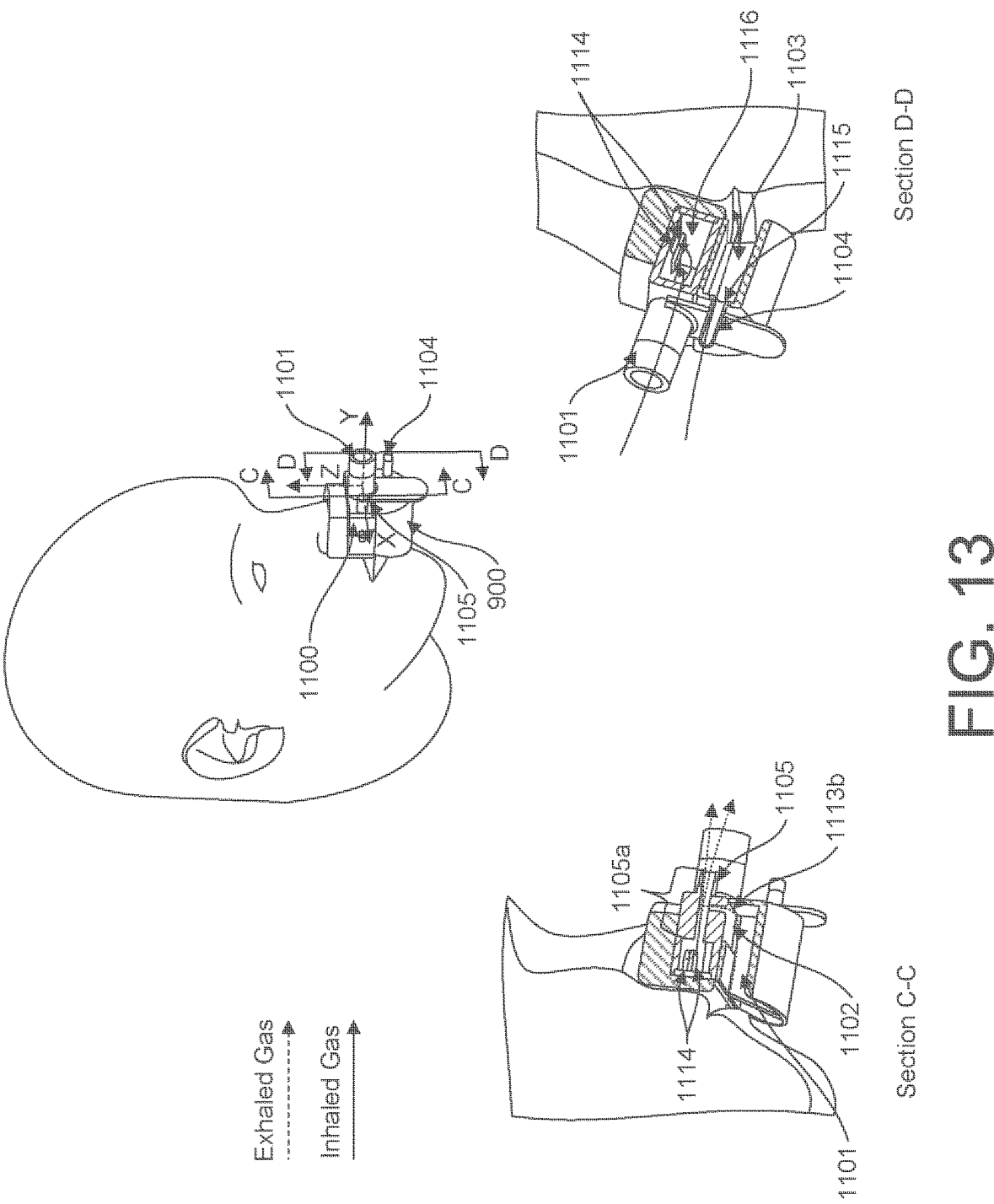
FIG. 13 are cross-sectional views illustrating a nasal respiratory apparatus with combined nasal/oral end tidal sample port and ventilation scoop with supplemental $O_2$ port.

FIG. 13 shows a cross-sectional view in the Y-Z plane along the end tidal sample port centerline, Section C-C, and along the supplemental $O_2$ port centerline, Section D-D. nasal and orally exhaled gases flowing to the end tidal sample channel and out the end tidal sample port are illustrated in Section C-C. orally exhaled gas flows into the ventilation chamber 1150, on to the ventilation chamber to nasal respiratory oral opening 1106b, into the oral opening 1113b to the end tidal sample channel and ultimately out the end tidal sample port to a Capnography sensor (not shown). nasally exhaled gas flows from the air chamber 1103 to the nasal opening 1113a to the end tidal sample channel, down the channel to the end tidal sample port 1105 and on to the capnography sensor (not shown).

Section D-D shows supplemental oxygen flowing through the supplemental $O_2$ port 1104, through the $O_2$ port opening to the $O_2$ chamber 1115, through the supplemental $O_2$ chamber to the patient's mouth, where it is inhaled. Primary gas flows to the patient through the gas connection port 1101 to the air chamber 1116 where it then flows through the nares port 1114 into the nasal pharynx of the patient. The patient can breathe nasally, orally or both simultaneously.

Figure 14:
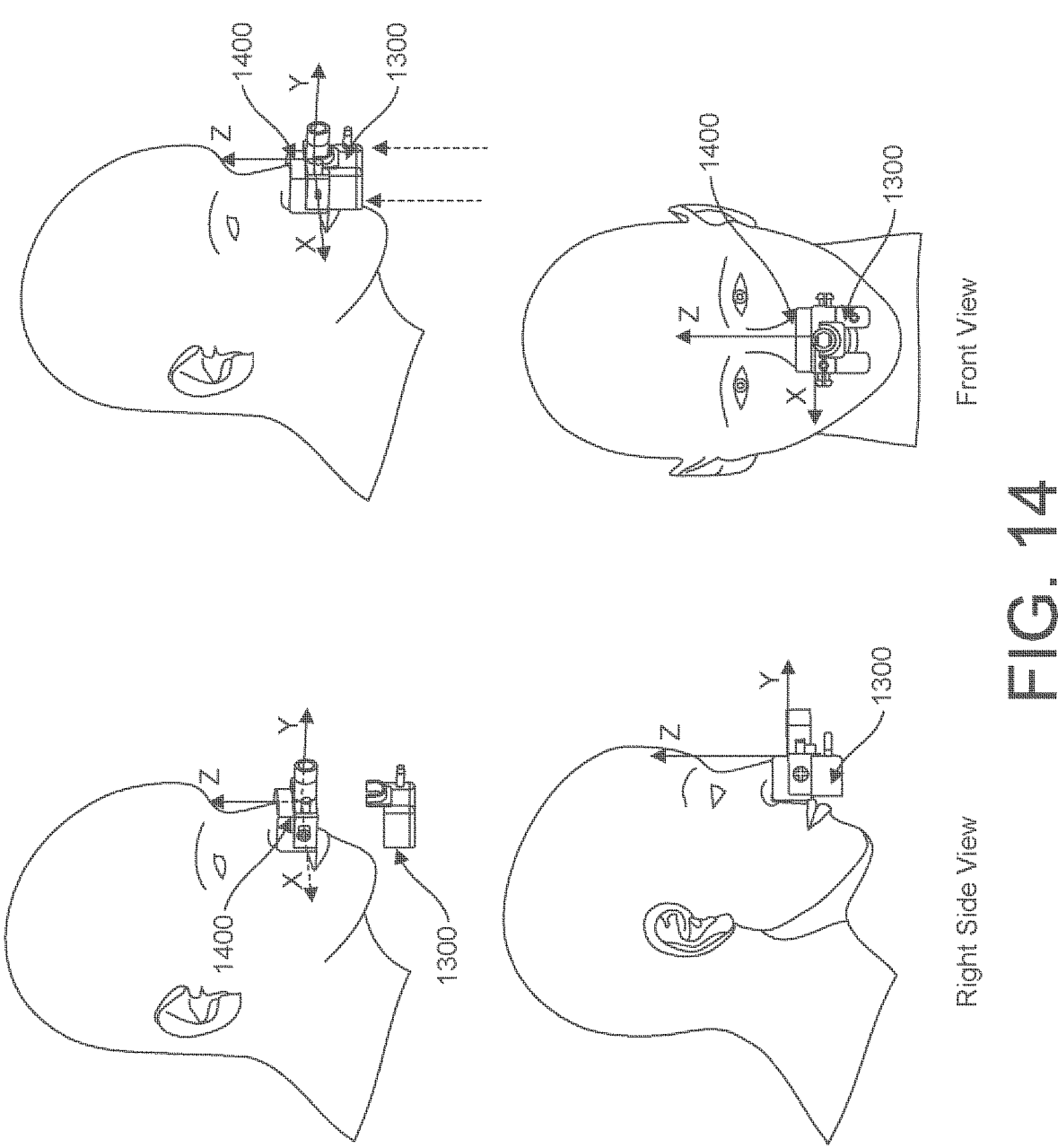
FIG. 14 illustrate a nasal respiratory apparatus with ventilation scoop and endoscope gap (gas connection port Parallel to Y-axis with Combined nasal and oral end tidal sample port).

Another embodiment of a system with nasal respiratory apparatus and ventilation scoop with a gas port parallel to the Y-axis is shown in FIG. 14, although the port could be parallel to the X or Z-axis. This configuration may be advantageous over the Z-axis configuration for patient access for different types of procedures in that it can be used with the patient in a supine position (laying on the back) or lateral position with the patient lying on the left or right side. As illustrated, a ventilation scoop 1300 may be separate from the nasal respiratory device 1400 and clip onto the gas connection port 1401 of the device 1400, one embodiment of which is illustrated in FIG. 14.

Figure 15:
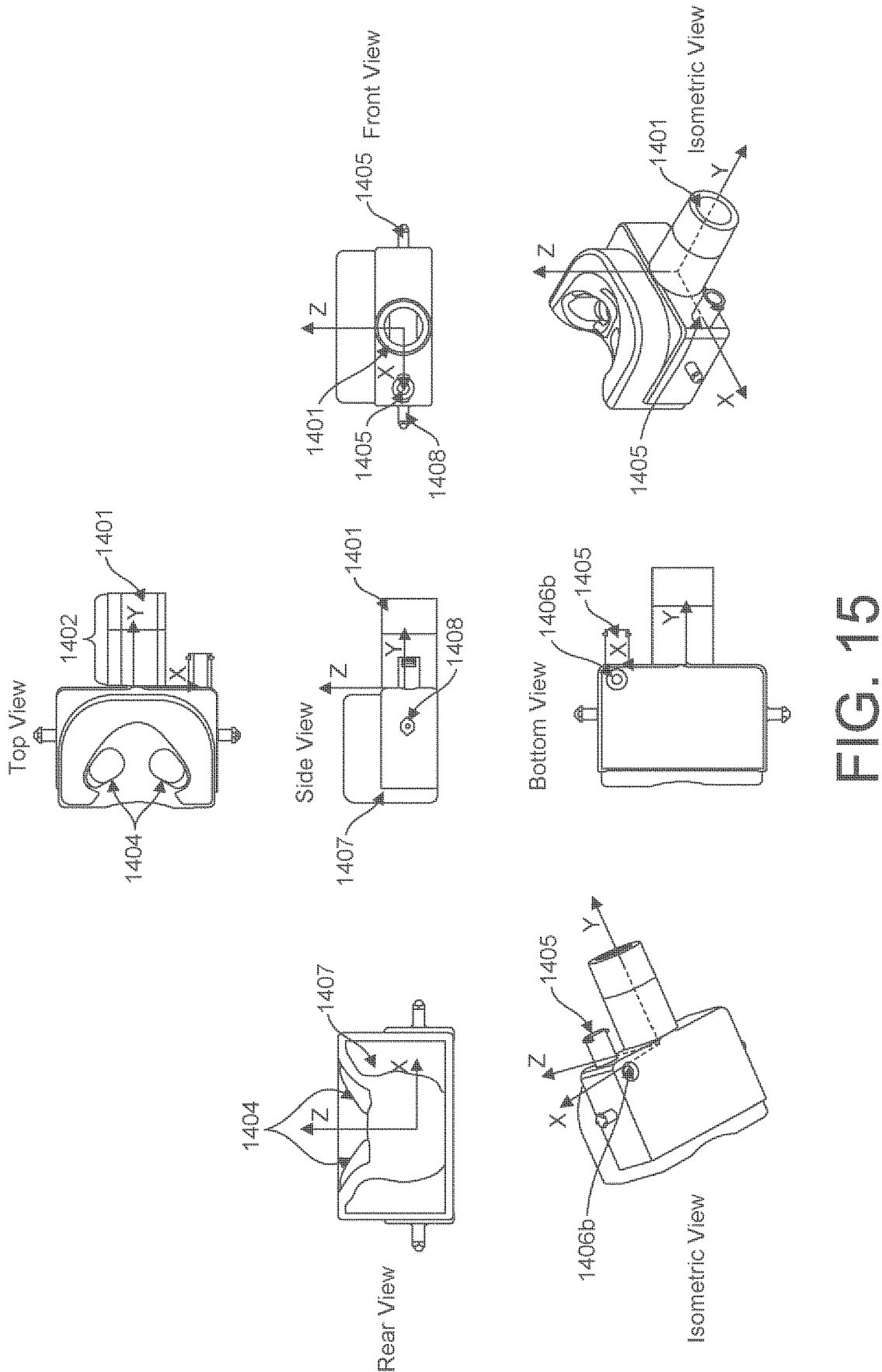
FIG. 15 illustrate a nasal respiratory apparatus (gas connection port Parallel to Y-axis).

Elements of the nasal respiratory apparatus configuration with the gas connection port 1401 parallel to the Y-axis are illustrated in FIG. 15, wherein the ventilation scoop 1300 includes a gap therein for passing an endoscope. An embodiment of the ventilation scoop with endoscopic gap is shown in more detail in FIG. 16. During the inhalation portion of the breathing cycle, pressurized gases (i.e., Oxygen ($O_2$), air anesthetic agents, etc.) are provided by a source (wall $O_2$ supply, bottled $O_2$ supply, ventilation machine, anesthesia machine, continuous positive airway pressure (CPAP) machine, bilevel positive airway pressure (BiPAP) machine, or another device). The pressurized gas enters the nasal respiratory apparatus via the gas connection port 1401, travels through the gas supply tube 1402 and the air chamber 1403 finally flowing out the nares ports 1404. gas leaves the nares ports 1404, traveling through the patient's nasal pharynx and eventually reaches the patient's lungs where it is absorbed into the blood stream. During the exhalation portion of the breathing cycle, waste $CO_2$ and unabsorbed gases are expelled from the lungs by pressure created by the diaphragm and ventilated in the opposite direction out of the lungs, thorough the nares ports 1404, traveling through the air chamber 1403, the gas supply tube 1402 and out the gas connection port 1401. A small amount of ventilated gas (i.e., carbon dioxide ($CO_2$), oxygen, anesthetic gases, etc.) can be sampled out of the single nasal/oral end tidal sample port 1405 by a monitoring device (not shown). If the patient exhales orally, gas from the mouth enters the oral ventilation scoop and enters the nasal/oral end tidal sample port 1405. The combined nasal and oral end tidal sample port 1405 is connected to a sample line (not shown) attached to a gas monitoring device (not shown). Additionally, a supplemental $O_2$ port is provided as part of the ventilation scoop where the supply line from an $O_2$ source can be plugged into a supplemental $O_2$ port, providing gases orally. An exemplary supplemental $O_2$ port is illustrated in FIG. 16 in combination with a ventilation scoop having an endoscope gap.

Figure 16:
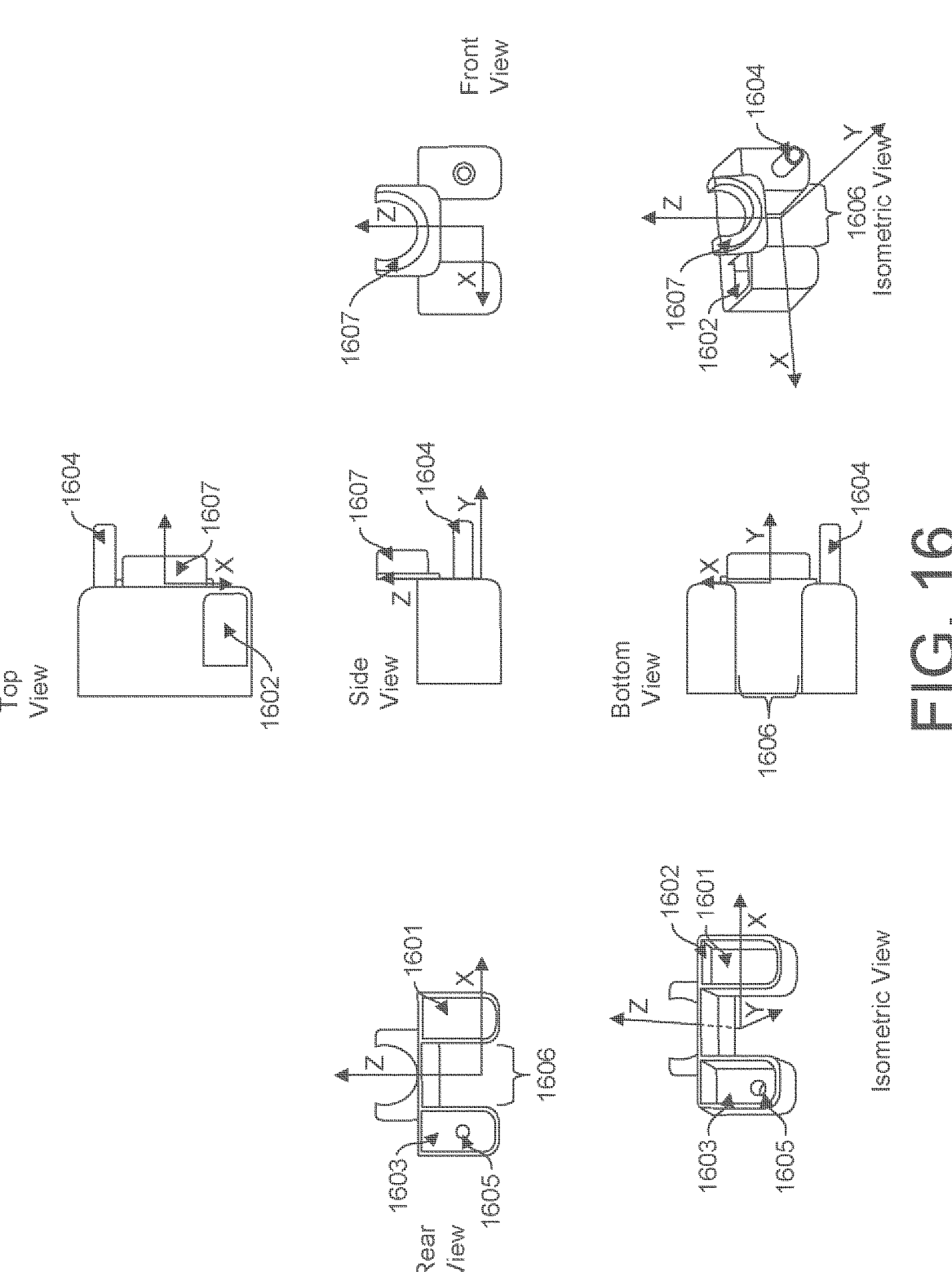
FIG. 16 illustrates a ventilation scoop, supplemental $O_2$ port and endoscope gap.

The ventilation scoop, supplemental $O_2$ port and endoscope gap 1600 are illustrated in FIG. 16. The ventilation scoop, supplemental $O_2$ port and endoscope gap fits onto the gas connection port (not shown) of the nasal respiratory device perhaps by snapping on, with a clasp or via interference fit or the like. The ventilation scoop, supplemental $O_2$ port and endoscope gap shown has two chambers separated by a gap 1606 that allows for the passage of an endoscope to the mouth of a patient. The ventilation chamber opening 1602 is located near the patient's mouth and channels exhaled gases towards the oral opening to the end tidal sample channel of the nasal respiratory apparatus (not shown). The ventilation chamber to nasal respiratory device oral opening 1602 of the ventilation scoop 1650 and the oral opening (not shown) of the nasal respiratory device may be coincident. If the patient is breathing orally, fresh gas is provided via the supplemental $O_2$ chamber 1603 with the opening located near the patient's mouth.

Figure 17:
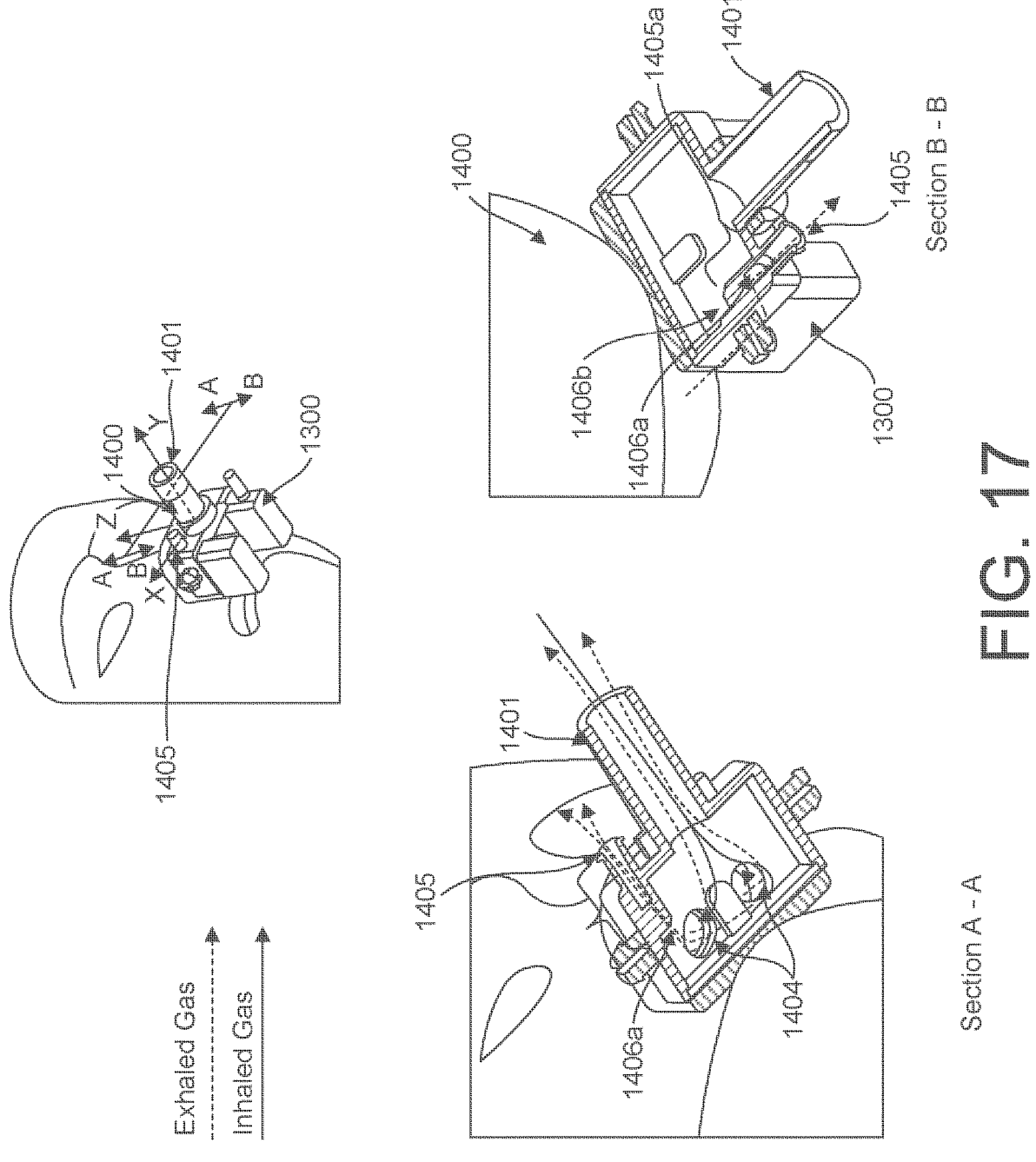
FIG. 17 are cross-sectional Views illustrating a nasal respiratory apparatus with combined nasal/oral end tidal sample port.

Referring to FIG. 17, gas port connection 1401 provides interface with standard $O_2$ source, anesthesia machine, hyper-inflation bag, high-flow source or ventilator 8.5 mm, 11.5 mm, 15 mm or 22 mm conical connectors as defined by ISO 5356 or current equivalent standard. Other connector interfaces are possible. This port is designed to fit male or female connectors. A male connection interface is shown on this illustration. Note the gas port connection 1401 can be located in either the plus or minus direction in an orientation with its axis parallel to the X, Y or Z-axis.

The gas supply tube 1402 is a conduit containing and allowing for the flow of gas between the gas connection port 1401 and the air chamber 1403. The gas supply tube 1402 can either be rigid or expandable. Being expandable will accommodate for different size heads and allow the tubing to expand and retract as patients move head up and down, side to side, or rotate. Air chamber 1403 provides the structural and gas flow interface between the gas supply tube 1402, the nares ports 1404 and the end tidal sampling port 1405. One or two nares ports 1404 provide the mechanical and gas flow interface between the nares and the nasal respiratory apparatus.

The nasal/oral end tidal sample port 1405 parallel to the Y-axis is an optional interface allowing for sampling of the end tidal $CO_2$, end tidal $O_2$, etc. level from nasal exhalation by a sampling device (not shown) such as a Capnography Sensor, an oxygen sensor, or gas analyzer. The port exterior may be a standard luer lock connector that interfaces with a sampling line per ISO 80396-7: 2016(E) or current equivalent. A male or female connector can be implemented, a female interface is shown in the illustration. Alternate interfaces can also exist. The end tidal sample port 1405 can be on the plus or minus X-axis side of the air chamber. The end tidal sample port 1405 can be on the plus or minus X or Z-axis side of the air chamber.

Referring to FIG. 17, the end tidal sample channel 1405a has an opening into the air chamber 1403 via the nasal opening to the end tidal sample channel 1406a and the oral scoop via an oral opening to the end tidal sample channel 1406b, where it then terminates at the port opening 1405. $CO_2$ exhaled nasally into the air chamber 1403 enters the end tidal sample channel 1405 via the nasal opening to the end tidal sample channel 1406a. $CO_2$ exhaled orally into the ventilation scoop and supplemental $O_2$ port ventilation chamber 1450 enters the end tidal sample channel 1405a via the ventilation chamber to nasal respiratory device oral opening of the ventilation scoop 1406b. A nasal dam 1407 surrounds the nares ports 1404 and interfaces with the soft tissue of the patient's nasal base, providing a pressure seal in order to contain airflow between the nasal pharynx and the nasal respiratory apparatus. Head strap connectors 1408 provide mechanical tie points between the nasal respiratory apparatus and a head strap that secures nasal respiratory apparatus to the patient's head.

This embodiment allows for sampling of $CO_2$ or other gases that are exhaled nasally and or orally. FIG. 17 shows cross-sections A-A and B-B of the nasal respiratory apparatus. The gas port 1401, nares ports 1404 and nasal opening to the nasal/oral end tidal sample port 1405 are all common to the air chamber 1403. The ventilation scoop and supplemental $O_2$ port 1300 routes exhalation to an opening below the air chamber, near the mouth opening, and the flow path is common to the basal/oral end tidal port 1405 by an oral opening 1406b to the end tidal sample port 1405 closer to an interface with the sample channel with a Luer connector. During the inspiratory portion of a breathing cycle, external gas enters the gas connection port 1401 into the air chamber 1403, where it then leaves the air chamber 1403 through the nares port 1404, entering the patient's nasal pharynx and ultimately into the lungs. This phase is illustrated by FIG. 17, Section A-A. During the expiratory phase of the breathing cycle, exhaled gasses can leave the lungs nasally, orally or both. If the gas leaves nasally as illustrated in FIG. 17, Section A-A, gas flows out the gas connection port 1401 and a portion also flows out the nasal opening to the end tidal sample channel 1406a then out the gas connection port 1401 if it is attached to a gas monitoring device (not shown). If the gas leaves orally as illustrated in FIG. 17, Section B-B, gas flows out the mouth and a portion also flows into the ventilation chamber 1450 of the ventilation scoop and supplemental $O_2$ port 1300, out the ventilation chamber to nasal respiratory apparatus oral opening and into the oral opening of the end tidal sample channel 1406b. It then leaves the channel and out the nasal/oral end tidal port 1405 if it is attached to a gas monitoring device (not shown).

Figure 18:
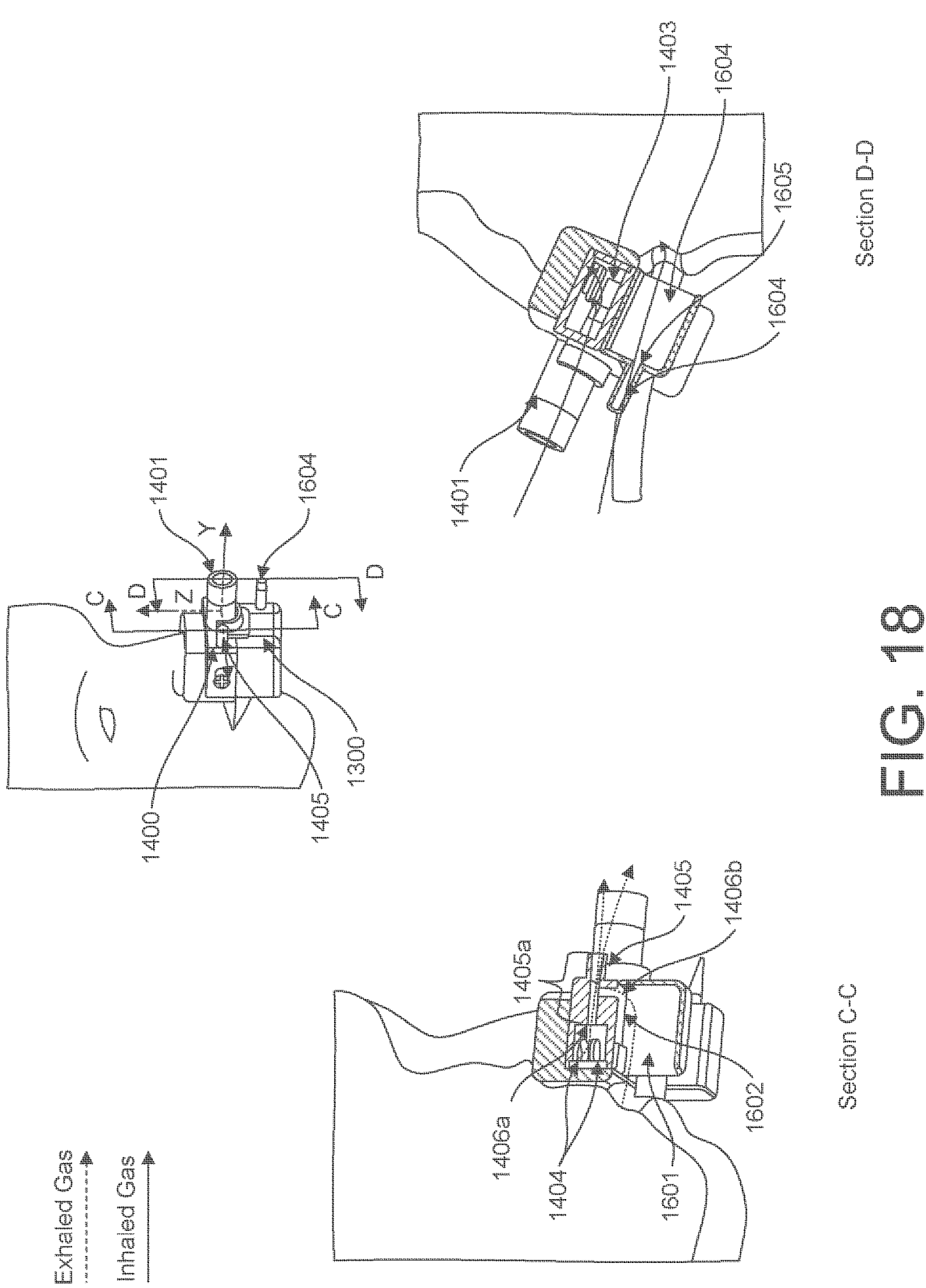
FIG. 18 are cross-sectional views illustrating a nasal respiratory apparatus with combined nasal/oral end tidal sample port and ventilation scoop with supplemental $O_2$ port.

FIG. 18 shows a cross-sectional view in the Y-Z plane along the portend tidal sample port 1405 centerline, Section C-C, and along the supplemental $O_2$ port 1604 Centerline, Section D-D. nasal and orally exhaled gases flowing to the end tidal Sample channel and out the portend tidal sample port are illustrated in Section C-C. orally exhaled gas flows into the ventilation chamber 1601, on to the ventilation chamber to nasal respiratory device oral opening 1602, into the oral opening to the end tidal sample channel 1406b and ultimately out the end tidal sample port 1405 to the Capnography sensor (not shown). nasally exhaled gas flows from the air chamber to the nasal opening to the end tidal sample channel 1406a, down the channel to the end tidal Sample port 1405 and on to the capnography sensor (not shown).

Section D-D shows supplemental oxygen flowing through the supplemental $O_2$ port 1604, through the $O_2$ port opening to the supplemental $O_2$ chamber 1605, through the supplemental $O_2$ chamber to the patient's mouth, where it is inhaled. Primary gas flows to the patient through the gas connection port 1401 to the air chamber 1403, where it then flows through the nares port 1404 into the nasal pharynx of the patient. The patient can breathe nasally, orally or both simultaneously.

Figure 19:
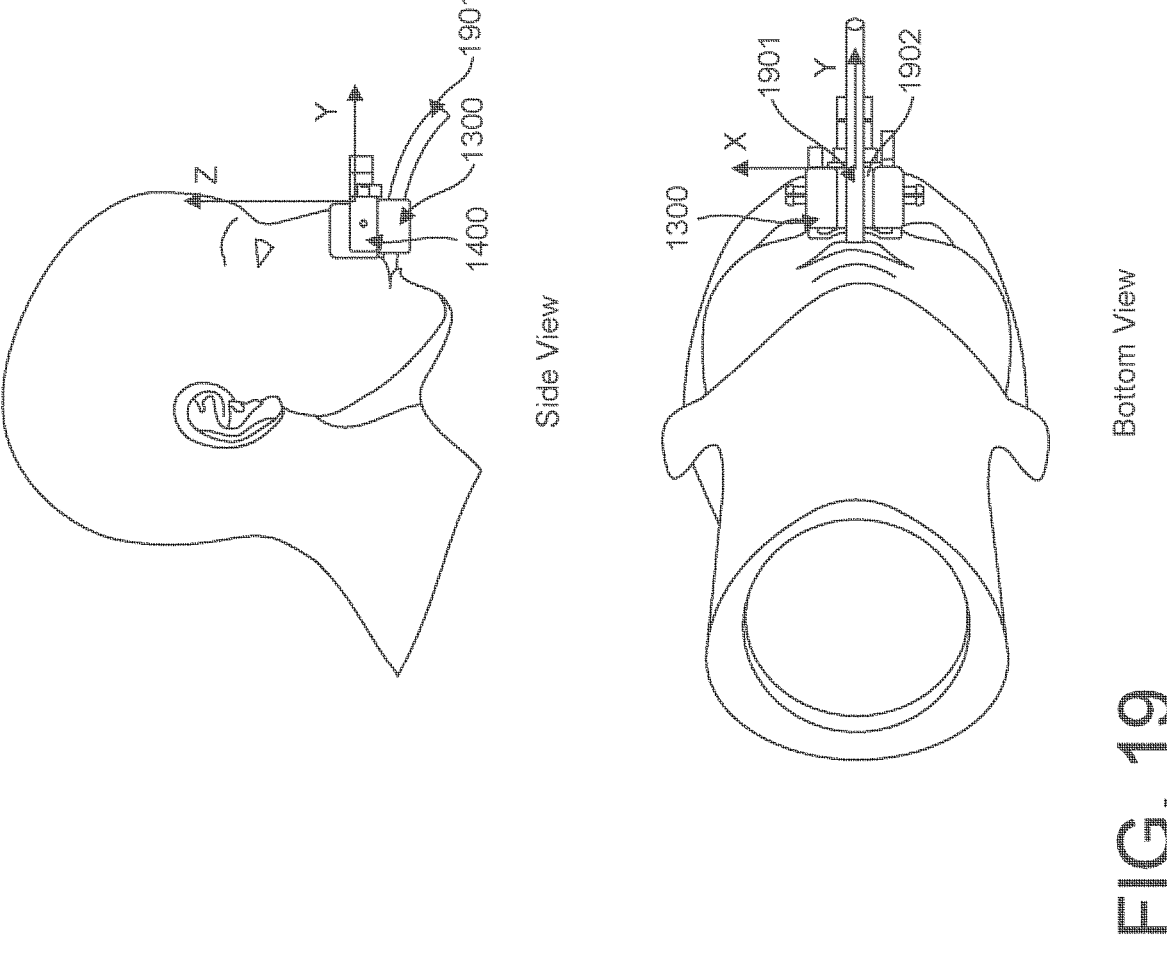
FIG. 19 illustrates an appliance with oral ventilation scoop, supplemental $O_2$ port and endoscope gap.
Figure 19:
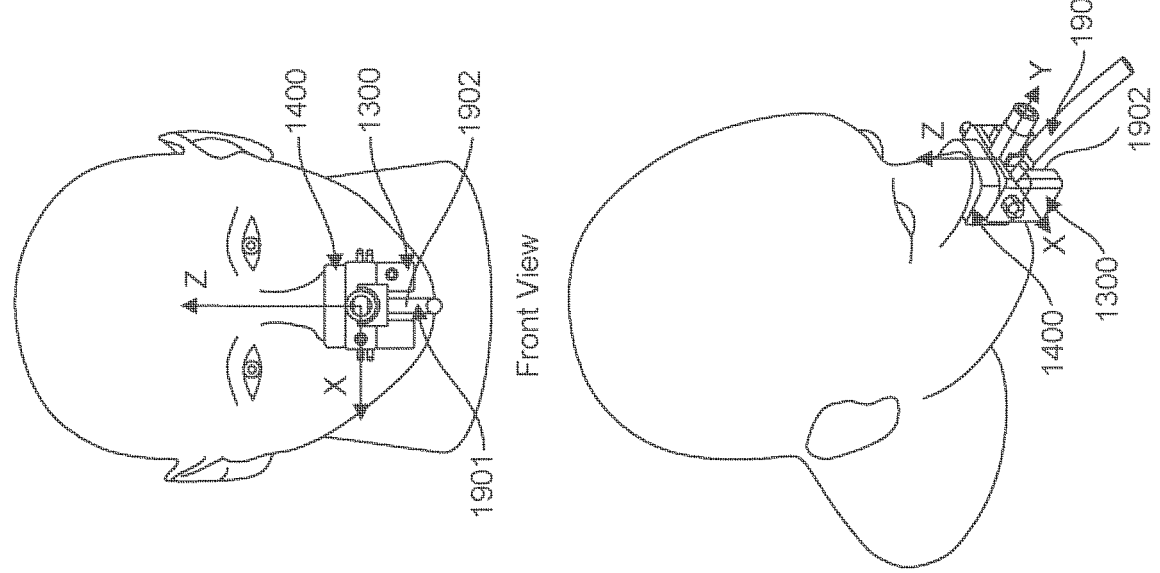

FIG. 19 provides multiple views of an endoscope 1901 being placed into the patient's mouth via the endoscope gap 1902. This allows for oral simultaneous oral $CO_2$ sampling, supplemental oral oxygen and endoscope use.

Referring to FIG. 16, The ventilation chamber 1601 has an opening near the patient's mouth and provides a channel to the oral opening to end tidal sample channel 1406s of the nasal respiratory device. The ventilation chamber to nasal respiratory apparatus oral opening 1602 is located on the chamber Top Wall 1610 of the ventilation chamber is designed to be coincident with the oral opening of the nasal respiratory device (not shown in FIG. 16) and allows exhaled gas to enter the oral opening of the nasal respiratory device. The supplemental $O_2$ chamber 1603 has an opening near the patient's mouth and allows for flow from the supplemental $O_2$ port to the patient who is breathing orally. The supplemental $O_2$ port 1604 is located on the chamber Front Wall of the supplemental $O_2$ chamber and connects to the supply line of an $O_2$ or air source. The $O_2$ port opening 1605 to $O_2$ chamber allows for gas flow between the supplemental $O_2$ port 1604 and the supplemental $O_2$ chamber 1603. The endoscope gap 1606 allows for passage of an endoscope to a patient's mouth while simultaneously sampling orally exhaled end tidal $CO_2$ and also providing supplemental $O_2$ orally. The nasal respiratory apparatus gas port clip 1607 secures the ventilation scoop and supplemental $O_2$ port 1600 to the nasal respiratory device. This occurs when the nasal respiratory apparatus gas port clip 1607 is forced onto the gas connection port 1401 of the device in the Z direction and the opening of the clip separates in the X-Z plane. As it continues to move in the Z direction, it wraps around the gas connection port 1401 and is clipped to the port 1401, securing it. The chamber Top Wall is then coincident with the bottom surface of the nasal respiratory device, preventing rotation about the Y-axis.

Figure 20:
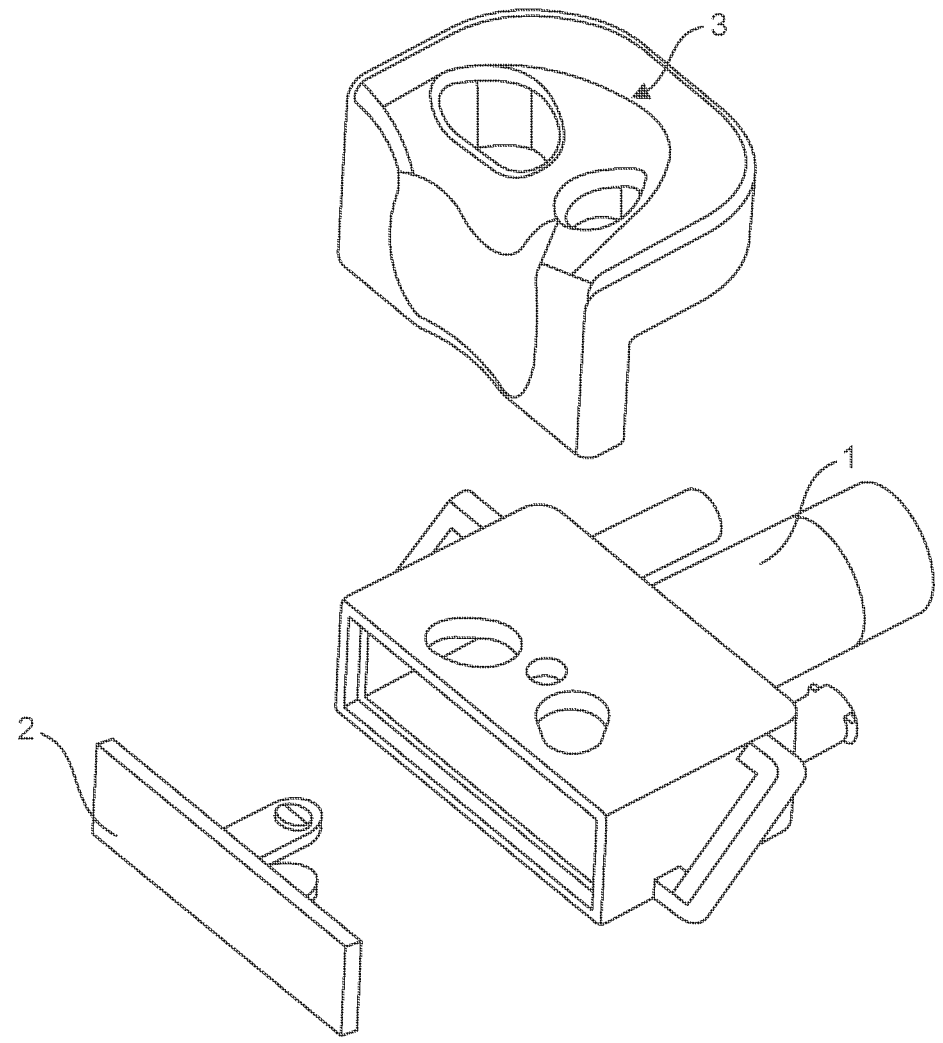
FIG. 20 illustrates three piece configuration a nasal respiratory apparatus related to principles described herein.

In an embodiment, an assembly/system according to principles described herein may nonexclusively include three parts, as illustrated in FIG. 20. The air chamber has an open end that is enclosed by snapping in the air chamber end cap into the opening. It is then covered by a soft nasal overmold or may include a separately removal nasal dam that overlies the nasal respiratory device and plugs into ports/openings that allow access to each gas through the upper wall 138 of the air chamber. As shown in FIG. 20, the device may have two such ports/opening that correspond to nares ports in the nasal dam (3, in FIG. 20).

Figure 21A:
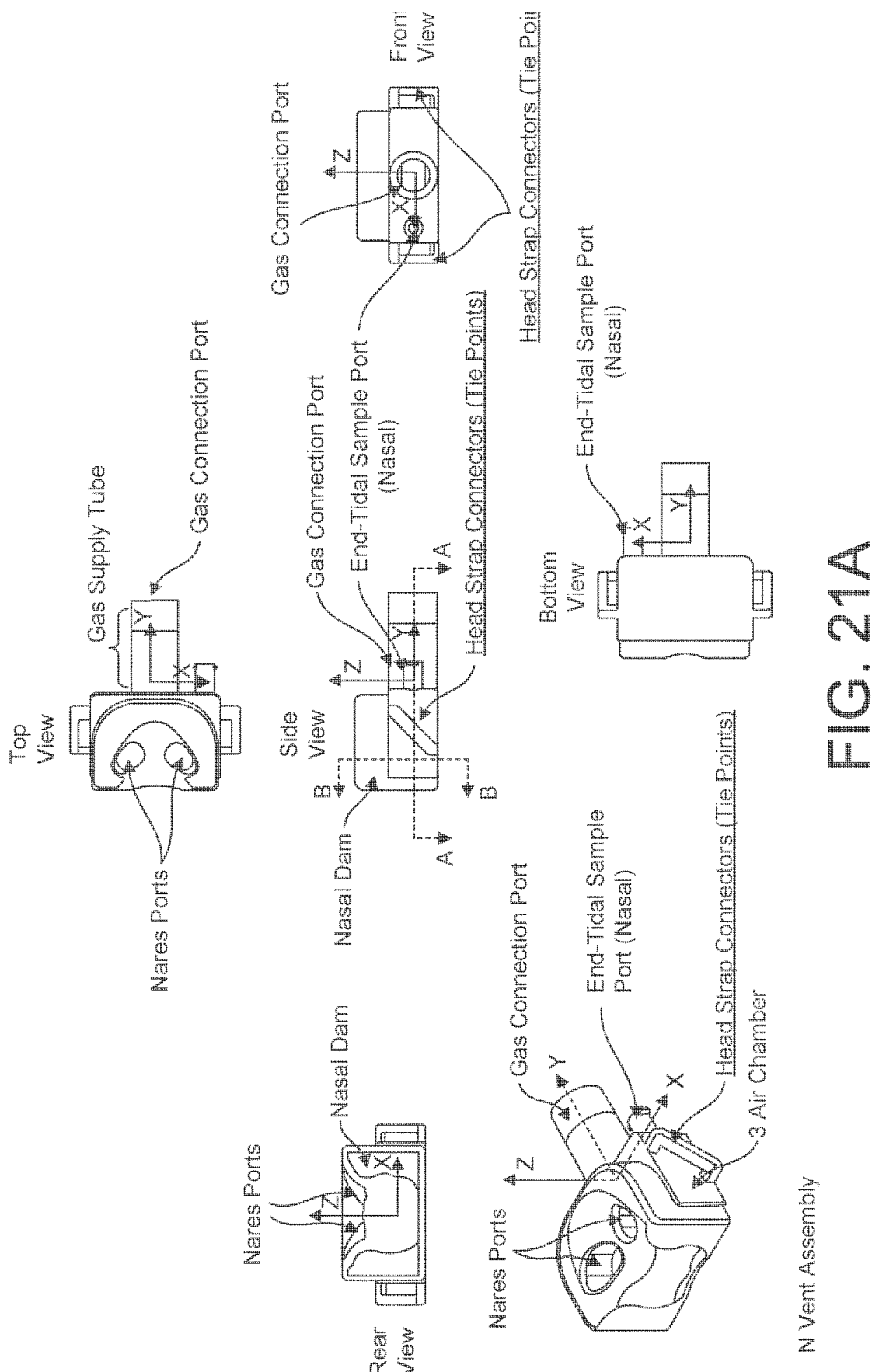
FIG. 21A illustrates an embodiment of the nasal respiratory apparatus related to principles described herein.
Figure 21B:
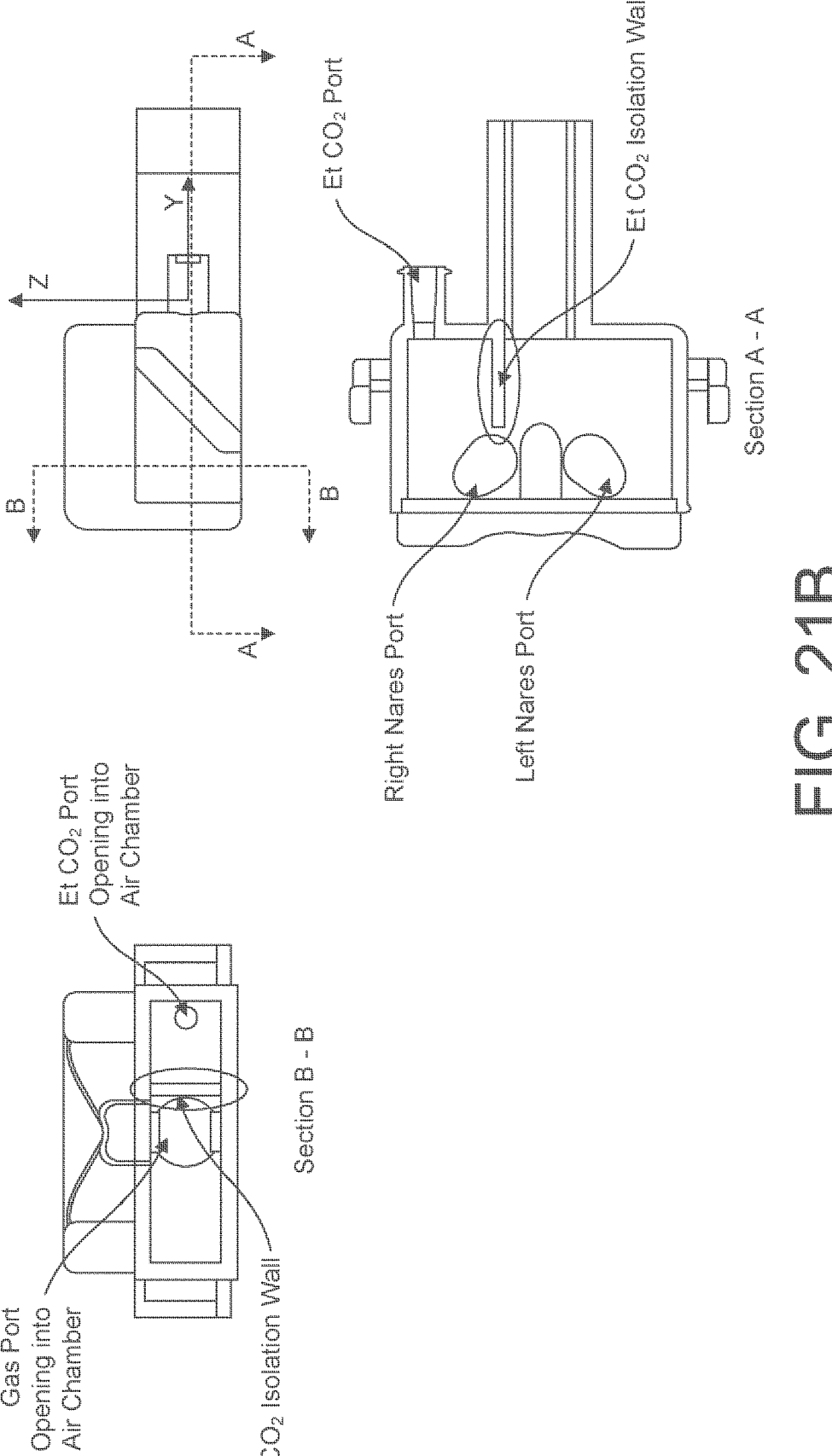
FIG. 21B illustrates an embodiment of the nasal respiratory apparatus with an isolation wall in an air chamber thereof.

Further detail of an assembly having three parts is illustrated in FIG. 21A. As illustrated, the air chamber has an open end that is enclosed by snapping in the air chamber end cap into the opening. It is then covered by a soft nasal cushion, which may be overmolded onto the exterior of the air chamber upper surface or may be a separate removable nasal dam. Elements of the present embodiment of the nasal respiratory apparatus are illustrated in FIG. 21B and include an air chamber, air chamber end cap, and nasal cushion. The material utilized to produce the assembly may be polypropylene, polystyrene, high impact polystyrene or equivalent for the air chamber structure interface and air chamber end cap. The nasal overmold may be made of any suitable material with a Shore A of 5-50. Such suitable material may include thermoplastic elastomers, silicone or any other material of appropriate Shore A.

The assembly includes has an $EtCO_2$ (end tidal $CO_2$) isolation wall to reduce the mixing of fresh gas from the gas port with exhaled gas from the right (or left) nares. The objective is to reduce mixing of fresh and inhaled gas in order to obtain a purer exhalation sample via the end tidal port as shown in the section views of FIG. 21B and FIG. 21C. FIG. 21B shows the $EtCO_2$ isolation wall, located in the Y-Z plane, extends between the top and bottom air chamber surfaces parallel to the X-Y plane. The wall thus creates a barrier between the gas port opening in the "left" half of the air chamber, section B-B where fresh gas enters the air chamber and the end tidal sample port opening in the "right" half of the chamber. The $EtCO_2$ isolation wall extends along the Y-axis from the right air chamber wall, ending at the right nares port opening as shown in section C-C.

Figure 21C:
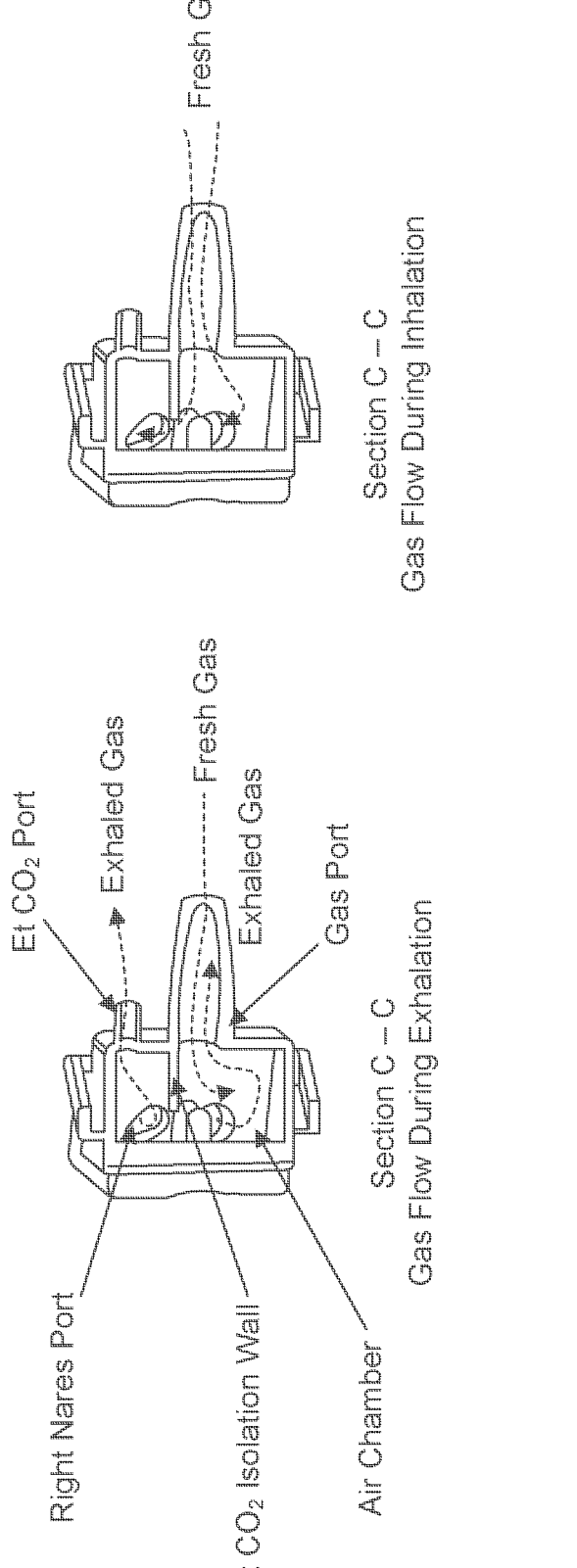
FIG. 21C illustrates a cross-sectional view and flow of expiratory gases that occurs during exhalation and inspiratory gases occurring during inspiration.

FIG. 21C shows a cross-sectional view, C-C, with a diagram of expiratory gas flow that occurs during exhalation and inspiratory gas flow occurring during inspiration. Fresh gas is always being provided to the patient via the gas port. During expiration, pressure derived from the patient's diaphragm expels consumed gas containing $CO_2$ through the right and left nares ports into the air chamber. If an $EtCO_2$ end tidal sample port is attached to a capnography machine sample vacuum line, gas expelled from the right nares port will flow through the $EtCO_2$ sample port and the $EtCO_2$ isolation wall will minimize any fresh gas that could be present, diluting the measurement. When the patient inhales fresh gas as shown in FIG. 21C, fresh gas can travel to both the right and left nares ports.

Any of the embodiments of the nasal respiratory device described herein may include $EtCO_2$ isolation wall that substantially isolates exhaled gas from fresh gas, as described with respect to FIGS. 21A-C and/or an $EtCO_2$ isolation wall that allows fresh gas to enter both the left and right nares of the patient during inhalation.

The isolation wall described with respect to FIGS. 21A, 21B and 21C may be included in any of the air chambers in any of the configurations described throughout this document. Exemplary descriptions of a nasal end tidal sample port are provided herein, or any other configuration of end tidal sample port described herein. Exemplary description of a gas connection port is provided herein, or any other configuration of the gas connection port described herein may be used in connection with the isolation wall described with reference to FIGS. 21A-C. Moreover, the gas connection port could also interface with a standard oxygen line. The apparatus described with respect to at least FIGS. 1A-3 may incorporate the air chamber of FIGS. 21A-C, for example, without limitation to the air chamber isolation wall's inclusion with other apparatuses described herein. For example, the isolation wall could be used in conjunction with the air chamber 2203 shown in FIG. 22, or any other appropriate air chamber described at various point throughout this document, for example, in FIGS. 23 and 24 Any disclosed $CO_2$ port, gas connection port, strap connectors, nasal dams, nasal interfaces, nares ports, forehead standoffs or the like may be used in conjunction with the air chamber configuration of FIGS. 21A-C.

In combination with the air chamber of FIG. 21, a gas port connection provides interface with standard $O_2$ source, anesthesia machine, hyper-inflation bag, high-flow source or ventilator, which may be via a standard 8.5 mm, 11.5 mm, 15 mm or 22 mm conical connectors as defined by ISO 5356 or current equivalent standard. Other connector interfaces are possible. This port is designed to fit male or female connectors. A male connection interface is shown on this illustration. The gas port connection can be located in either the plus or minus direction in an orientation with its axis parallel to the X, Y or Z-axis. The gas connection port may connect to a CPAP or BiPAP.

The gas supply tube is a conduit containing and allowing for the flow of gas between the gas connection port and the air chamber, which includes an isolation wall therein such that there is a barrier between the gas port opening in the "left" half of the air chamber, section B-B where fresh gas enters the air chamber, and the end tidal sample port opening in the "right" half of the chamber. The $EtCO_2$ isolation wall extends along the Y-axis from the right air chamber wall, ending at the right nares port opening as shown in section C-C. The gas supply tube can either be rigid or expandable. Being expandable will accommodate for different size heads and allow the tubing to expand and retract as patients move head up and down, side to side, or rotate. Air chamber provides the structural and gas flow interface between the gas supply tube, at least one nares ports and the end tidal sample port. One or two nares ports provide the mechanical and gas flow interface between the nares and the nasal respiratory apparatus. The portend tidal sample port is an optional interface allowing for sampling of the end tidal $CO_2$, etc. level from nasal exhalation by a sampling device such as a Capnography Sensor, an oxygen sensor, or gas analyzer (not shown). The port exterior may be a standard luer lock connector that interfaces with a sampling line per ISO 80396-7: 2016(E) or current equivalent. A male or female connector can be implemented, a female interface is shown in the illustration. Alternate interfaces can also exist. The end tidal sample port can be on the plus or minus X-axis side of the air chamber.

The nasal dam surrounds the nares ports and interfaces with the soft tissue of the patient's nasal base, providing a pressure seal in order to contain airflow between the nasal pharynx and the nasal respiratory apparatus. Connection pins allow for interface with either an orally exhaled end tidal $CO_2$ sampling connection, or a bite block or other desired modular component. Head strap connectors provide mechanical tie points between the device and a head strap (not shown) that secures the nasal respiratory apparatus to the patient's head.

Figure 22:
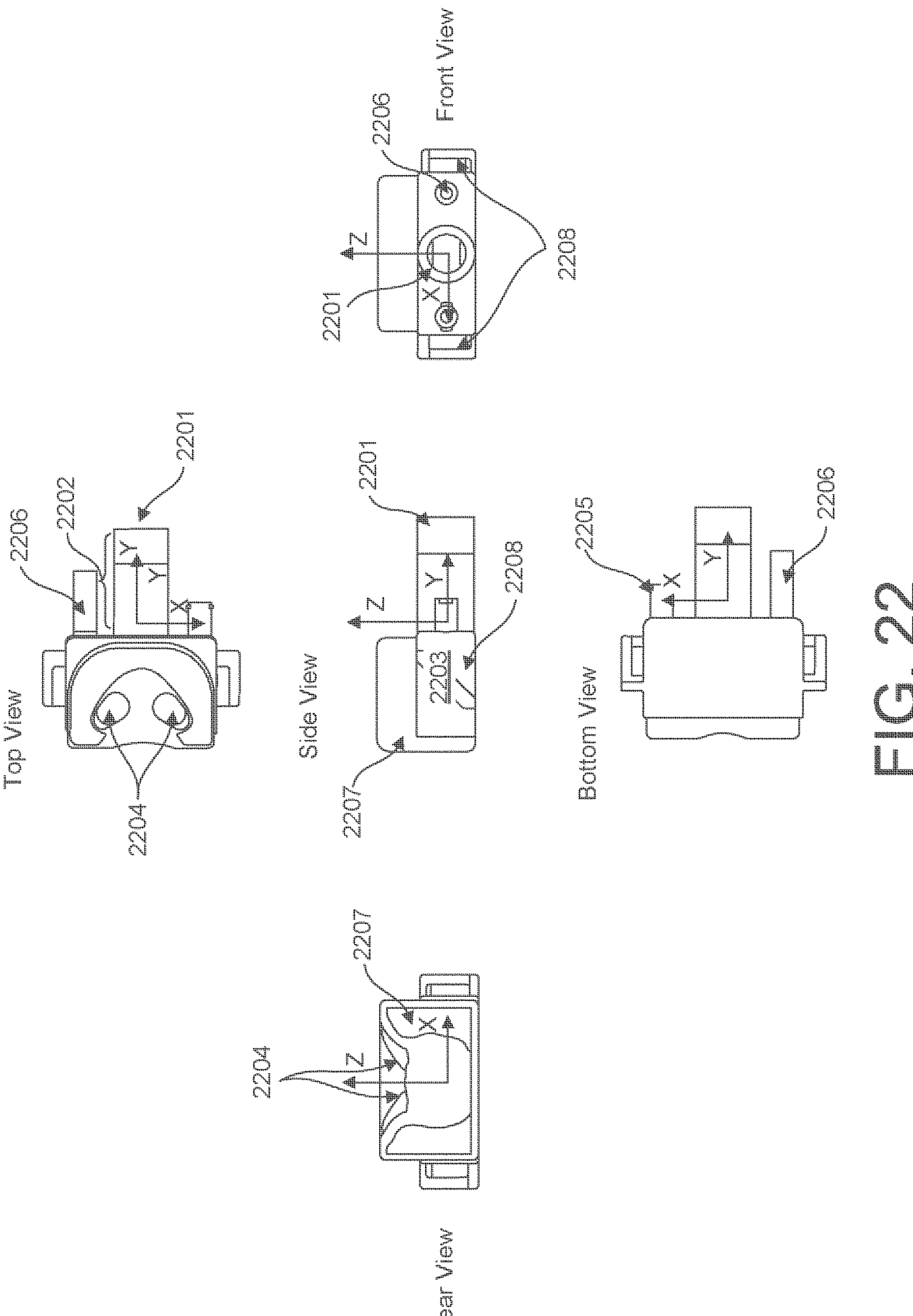
FIG. 22 illustrates a nasal respiratory apparatus with a nasal dam.

Additional description of an assembly according to principles described herein are made with reference to FIG. 22. A gas port connection 2201 provides an exemplary interface, which may include a 15 mm conical connector as defined by ISO 5356-1:2015(E). A gas supply tube 2202 is a conduit containing and allowing for the flow of gas between the gas connection port 2201 and an air chamber 2203. Air chamber 2203 provides the structural and gas flow interface between the gas supply tube 2202, at least one nares ports 2204 and an end tidal sample port 2205.

One or two nares ports 2204 provide the mechanical and gas flow interface between the nares and the nasal respiratory chamber. The nasal end tidal sample port 2205 being parallel to the X or Y-axis supports sampling of the end tidal $CO_2$. In the case of the extension of the X axis, the end tidal sample port could extend from either face of the air chamber parallel to the X-Z plane. It could also be parallel to the Z-axis, extending from either face of the air chamber parallel to the X_Y plane. The port exterior may be a female luer slip connector is per ISO 80396-7: 2016(E). supplemental $O_2$ port 2206 allows for the supply of supplemental $O_2$ via an $O_2$ line (not shown).

A nasal dam 2207 may surround the nares ports 2204 and interface with the soft tissue of a patient's nasal base, providing a pressure seal in order to contain airflow between the patient's nasal pharynx and the nasal respiratory device. Head strap connectors (tie points) 2208 provide mechanical tie points between the device and the head strap that secures the device to the patient's head.

Figure 23:
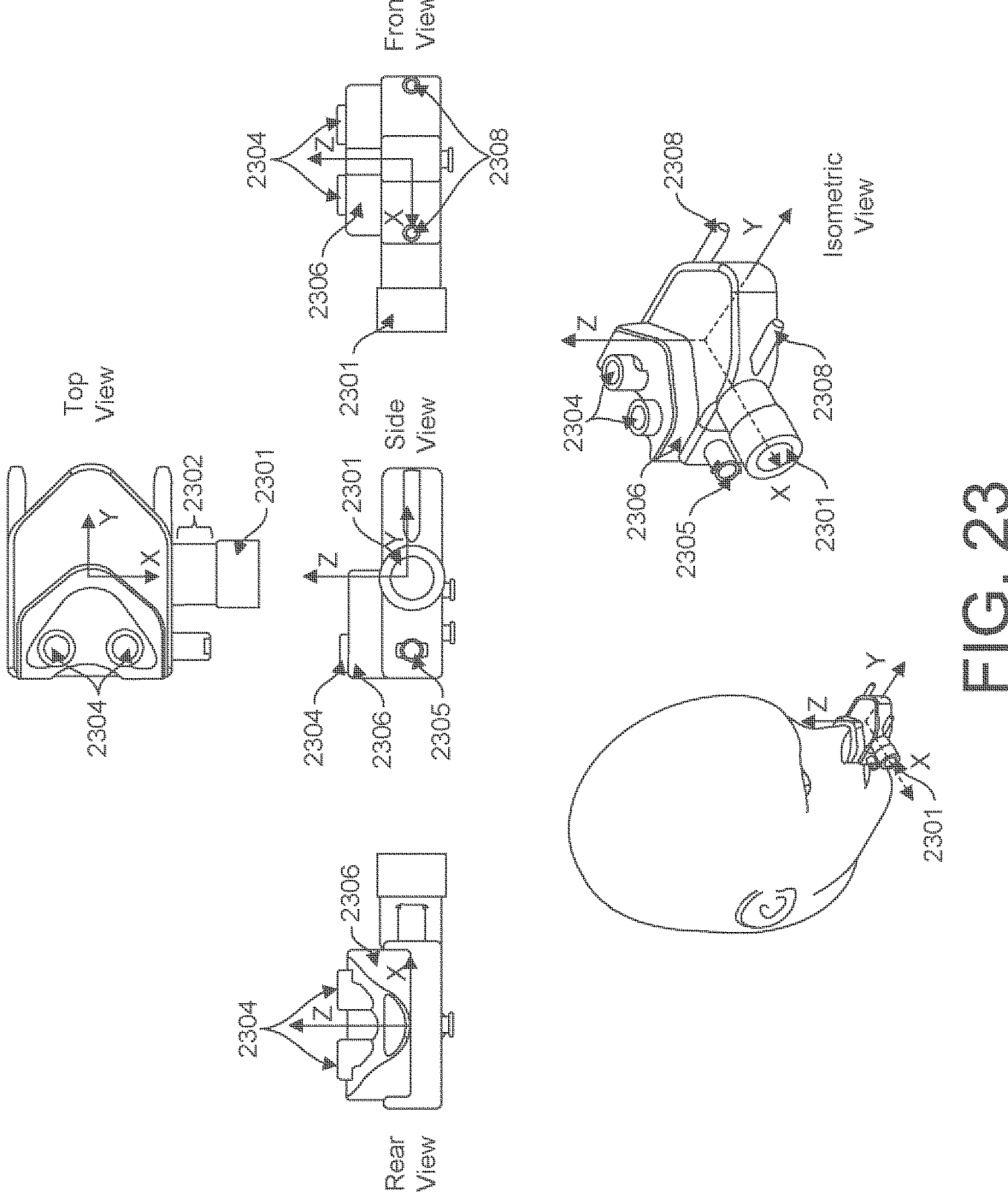
FIG. 23 illustrates a nasal respiratory apparatus with a nasal dam and with gas port parallel to the X-axis.
Figure 24:
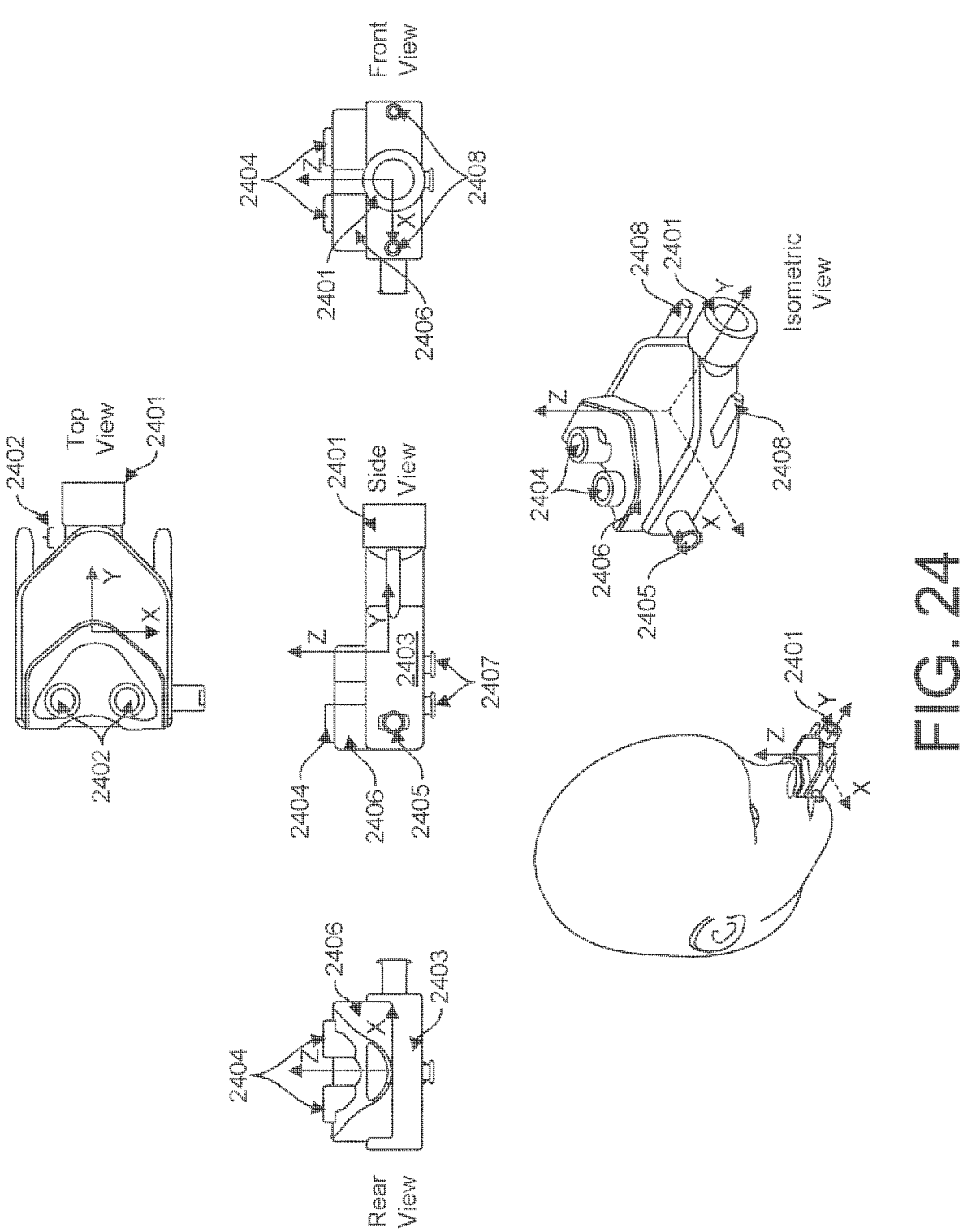
FIG. 24 illustrates a nasal respiratory apparatus with a nasal dam and with gas port parallel to the Y-axis.

Elements of the nasal respiratory apparatus for configurations with the gas connection port parallel to the X-axis and parallel to the Y-axis are illustrated in FIG. 23 and FIG. 24 respectively. Except for the gas port connection axes orientation, both configurations have the same elements, as described herein. During the inhalation portion of the breathing cycle, pressurized gases (i.e., Oxygen ($O_2$), air anesthetic agents etc.) are provided by a source (wall $O_2$ supply, bottled $O_2$ supply, ventilation machine, anesthesia machine continuous positive airway pressure (CPAP) machine, or another device). The pressurized gas enters the nasal respiratory apparatus via the gas connection port 2301/2401, travels through the gas supply tube 2302/2402 and the air chamber 2303/23403 finally flowing out the nares ports 2304/2404. gas leaves the nares ports 2304/2404, traveling through the patient's nasal pharynx and eventually reaches the patient's lungs where it is absorbed into the blood stream. During the exhalation portion of the breathing cycle, waste $CO_2$ and unabsorbed gases are expelled from the lungs by pressure created by the diaphragm and ventilated in the opposite direction out of the lungs, thorough the nares ports 2304/2404, traveling through the air chamber 2303/2403, the gas supply tube 2302/2402 and out the gas connection port 2301/2401. A small amount of ventilated gas (i.e. carbon dioxide $CO_2$), oxygen, anesthetic gases, etc.) can be sampled out of the portend tidal sample port 23052/2405 by a monitoring device (not shown).

Gas port connection 2301/2401 provides interface with standard $O_2$ source, anesthesia machine, hyper-inflation bag, high-flow source or ventilator, which may be via a standard 8.5 mm, 11.5 mm, 15 mm or 22 mm conical connectors as defined by ISO 5356 or current equivalent standard. Other connector interfaces are possible. This port is designed to fit male or female connectors. A male connection interface is shown on this illustration. The gas port connection 2301/2401 can be located in either the plus or minus direction in an orientation with its axis parallel to the X, Y or Z-axis.

The gas supply tube 2302/2402 is a conduit containing and allowing for the flow of gas between the gas connection port 2301/2401 and the air chamber 2303/2403. The gas supply tube 2302/2402 can either be rigid or expandable.

Being expandable will accommodate for different size heads and allow the tubing to expand and retract as patients move head up and down, side to side, or rotate. Air chamber 2303/2403 provides the structural and gas flow interface between the gas supply tube, at least one nares ports 2304/2404 and the end tidal sample port 2305/2405. One or two nares ports 2304/2403 provide the mechanical and gas flow interface between the nares and the nasal respiratory apparatus. The portend tidal sample port 2305/2405 is an optional interface allowing for sampling of the end tidal $CO_2$, etc. level from nasal exhalation by a sampling device such as a Capnography Sensor, an oxygen sensor, or gas analyzer (not shown). The port exterior may be a standard luer lock connector that interfaces with a sampling line per ISO 80396-7: 2016(E) or current equivalent. A male or female connector can be implemented, a female interface is shown in the illustration. Alternate interfaces can also exist. The end tidal sample port 2305/2405 can be on the plus or minus X-axis side of the air chamber 2303/2403.

The nasal dam 2306/2406 surrounds the nares ports 2304/2404 and interfaces with the soft tissue of the patient's nasal base, providing a pressure seal in order to contain airflow between the nasal pharynx and the nasal respiratory apparatus. connection pins 2307/2407 allow for interface with either an orally exhaled end tidal $CO_2$ sampling connection, or a bite block or other desired modular component. Head strap connectors 2308/2408 provide mechanical tie points between the device and a head strap (not shown) that secures the nasal respiratory apparatus to the patient's head.

While various embodiments of the present invention have been described above, it should be understood that they have been presented by way of example only, and not limitation. It will be apparent to persons skilled in the relevant art that various changes in form and detail can be made therein without departing from the spirit and scope of the present invention. Thus, the breadth and scope of the present invention should not be limited by any of the above-described exemplary embodiments, but should be defined only in accordance with the following claims and their equivalents.

What is claimed is:

1. A nasal respiratory apparatus comprising:
   an air chamber having a gas connection port, at least one nasal conduit, a nasal end tidal sample port, wherein the air chamber comprises an air chamber structure having an upper wall, a lower wall spaced from the upper wall, a pair of side walls, and a front end wall, wherein the side walls, the lower wall, and the upper wall define a rear opening opposite the front wall, wherein the upper wall defines the at least one nasal conduit, wherein the gas connection port is configured to receive an externally supplied gas via a gas supply tube and wherein the at least one nasal conduit is in fluid communication with the gas connection port; and
   a nasal dam comprising a nasal base portion and a nasal dam wall extending transversely from the nasal base portion, the nasal base portion having at least one nares port corresponding to the at least one nasal conduit of the air chamber, the nares port extending from an upper external surface of the nasal base portion to a lower external surface of the nasal base portion such that the lower external surface of the nasal base portion is supported on the upper wall of the air chamber and the upper external surface of the nasal base portion is configured to interface with soft tissue of a patient's nasal base to provide a substantial seal around the patient's nasal base, wherein the nasal dam wall is configured to engage the rear opening to substantially fluidically seal the rear opening of the air chamber.

2. The nasal respiratory apparatus of claim 1, wherein the air chamber and nasal dam are under compression such that the nasal dam is engaged with the air chamber.

3. The nasal respiratory apparatus of claim 1, the nasal dam having one or more first complementary engagement members at the lower external surface of the nasal base portion, the air chamber further comprising one or more second complementary members formed on the upper wall of the air chamber and corresponding to the one or more first complementary engagement members to engage with the one or more first complementary engagement members to align the at least one nares port with the at least one nasal conduit.

4. The nasal respiratory apparatus of claim 3, wherein the one or more first complementary engagement members includes a female dovetail slot in the lower external surface of the nasal base portion and the one or more second complementary engagement members includes a male dovetail slide extending from the upper wall of the air chamber.

5. The nasal respiratory apparatus of claim 3, wherein the one or more first complementary engagement members includes a male dovetail slide extending from the lower external surface of the nasal base portion and the one or more second complementary engagement members includes a female dovetail slot in the upper wall of the air chamber.

6. The nasal respiratory apparatus of claim 3, wherein the one or more first complementary engagement members includes a female hole in the lower external surface of the nasal base portion and the one or more second complementary engagement members includes a male post extending from the external upper surface of the air chamber.

7. The nasal respiratory apparatus of claim 3, wherein the one or more first complementary engagement members includes a male post extending from the lower external surface of the nasal dam and the one or more second complementary engagement members includes a female hole in the upper wall of the air chamber.

8. The nasal respiratory apparatus of claim 1, wherein the nasal dam wall comprises at least one air chamber plug extending therefrom, the at least one air chamber plug corresponding to the rear opening of the air chamber, wherein upon insertion of the at least one air chamber plug into the rear opening of the air chamber, the air chamber rear opening is substantially fluidically sealed.

9. The nasal respiratory apparatus of claim 8, wherein the at least one air chamber plug further comprises a nasal dam lock and an internal surface of the air chamber comprises a corresponding air chamber lock member for engaging the nasal dam lock.

10. The nasal respiratory apparatus of claim 9, wherein the nasal dam lock is a protrusion extending from a surface of the at least one air chamber plug and the corresponding air chamber lock member is a detent or opening in the internal surface of the air chamber.

11. The nasal respiratory apparatus of claim 9, wherein the nasal dam lock is a detent in a surface of the at least one air chamber plug and the corresponding air chamber lock member is a protrusion extending from the internal surface of the air chamber.

12. The nasal respiratory apparatus of claim 1, wherein the nasal end tidal sample port in fluid communication with the at least one nasal conduit for receiving sample nasal gas from the at least one nasal conduit and cause the sample nasal gas to exit the air chamber.

13. The nasal respiratory apparatus of claim 1, wherein the air chamber is a substantially closed chamber expect for the gas connection port, the at least one nasal conduit and, the nasal end tidal sample port.

14. The nasal respiratory apparatus of claim 1, further comprising an isolation wall in the air chamber, the isolation wall substantially separating the externally supplied gas from a nasally exhaled gas to be sampled via the end tidal port in the air chamber.

15. The nasal respiratory apparatus of claim 1, wherein the gas supply tube extends from the gas connection port external to the air chamber, the gas supply tube parallel to one of an X-axis, Y-axis or Z-axis.

16. The nasal respiratory apparatus of claim 1, wherein a gas flow path when worn by a patient and connected to an external gas supply comprises:

inhaled gas flows from the external gas supply through the gas supply tube through the gas connection port into the air chamber and through the nasal conduit to the patient's nares; and exhaled gas flows from the patient's nares through the nasal conduit into the air chamber and through the gas connection port through the gas supply tube and through the nasal conduit into the air chamber and to the nasal end tidal sample port.

17. The nasal respiratory apparatus of claim 16, wherein the exhaled gas passes through the nasal end tidal sample port to an external sample device.

18. The nasal respiratory apparatus of claim 1, further comprising connection pins extending from an external lower surface of the air chamber.

19. The nasal respiratory apparatus of claim 1, further comprising an oral end tidal scoop removably connected to the air chamber, the oral end tidal scoop having an oral end tidal sampling port.

20. The nasal respiratory apparatus of claim 19, further comprising a connection clip connected to the oral end tidal scoop and complementary to a profile of the gas supply tube extending from the gas connection port external to the air chamber such that the clip removably attaches to the gas supply tube with an interference fit.

21. The nasal respiratory apparatus of claim 19, further comprising the oral end tidal scoop having a first chamber and a second chamber, with an external gap between the first chamber and the second chamber, the gap sized to receive an endoscope therethrough.

22. The nasal respiratory apparatus of claim 19, wherein the oral end tidal scoop is fluidically isolated from the air chamber.

23. The nasal respiratory apparatus of claim 19, wherein the oral end tidal scoop is removably attached to the external lower surface of the air chamber via connection pins.

24. The nasal respiratory apparatus of claim 19, wherein a gas flow path when worn by a patient and connected to an external gas supply comprises:

exhaled gas flows from the patient's mouth into the oral end tidal scoop and to the oral end tidal sample port.

25. The nasal respiratory apparatus of claim 24, wherein the exhaled gas passes through the oral end tidal sample port to an external sample device.

26. The nasal respiratory apparatus of claim 1, further comprising a head strap, the head strap connected to external side walls of the air chamber.

27. The nasal respiratory apparatus of claim 26, further comprising strap connectors on respective ones of the external side walls of the air chamber for connecting the head strap to the external side walls of the air chamber.

28. The nasal respiratory apparatus of claim 26, wherein the head strap comprises a left strap and a right strap for extending over respective ones of a patient's ears.

29. The nasal respiratory apparatus of claim 26, further comprising an elastic split strap segment having an upper strap component and a lower strap component extending from a left junction and a right junction, the left strap connecting the upper strap component and the lower strap component at the left junction and the right strap connecting to the upper strap component and the lower strap component at the right junction.

30. The nasal respiratory apparatus of claim 26, the head strap comprising a center elastic loop band and two hook straps, a first of the two hook straps attached to a first side of the elastic loop band and a second of the two hook straps attached to a second side of the elastic loop band.

* * * * *